(12) United States Patent
Bjorkesten et al.

(10) Patent No.: US 9,383,335 B2
(45) Date of Patent: Jul. 5, 2016

(54) ELECTROPHORESIS GEL CASSETTE

(71) Applicant: GE HEALTHCARE BIO-SCIENCES AB, Uppsala (SE)

(72) Inventors: Lennart Bjorkesten, Uppsala (SE); Owe Salven, Uppsala (SE); Camilla Larsson, Uppsala (SE); Erik J Bjerneld, Uppsala (SE); Sofia Edlund, Uppsala (SE); Henrik Ostlin, Uppsala (SE); Stefan Sjolander, Uppsala (SE); Kajsa Stridsberg-Friden, Uppsala (SE); Ola Ronn, Uppsala (SE); Peter Oliviusson, Uppsala (SE); Henrik Bjorkman, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 0 days.

(21) Appl. No.: 14/403,613

(22) PCT Filed: May 31, 2013

(86) PCT No.: PCT/SE2013/050634
§ 371 (c)(1),
(2) Date: Nov. 25, 2014

(87) PCT Pub. No.: WO2013/180640
PCT Pub. Date: Dec. 5, 2013

(65) Prior Publication Data
US 2015/0185181 A1    Jul. 2, 2015

(30) Foreign Application Priority Data

May 31, 2012    (SE) ........................................ 1250560

(51) Int. Cl.
*G01N 27/453*    (2006.01)
*G01N 27/447*    (2006.01)

(52) U.S. Cl.
CPC ........ *G01N 27/447* (2013.01); *G01N 27/44704* (2013.01); *G01N 27/44756* (2013.01)

(58) Field of Classification Search
CPC .................. G01N 27/44756; G01N 27/44782; G01N 27/453
See application file for complete search history.

(56) References Cited

U.S. PATENT DOCUMENTS 3,888,759 A * 6/1975 Elson ............... G01N 27/44773
                                                          204/620
4,246,222 A    1/1981 Monthony
(Continued)

FOREIGN PATENT DOCUMENTS

WO    96/34276 A1    10/1996

OTHER PUBLICATIONS

PCT/SE2013/050634 ISRWO Dated Oct. 23, 2013.
European Supplementary Search Report for EP Application No. 13797203.0 mailed Apr. 20, 2016 (4 pages).

*Primary Examiner* — Alexander Noguerola
(74) *Attorney, Agent, or Firm* — Sutherland Asbill & Brennan LLP

(57) ABSTRACT

Electrophoresis gel cassette comprising a first and a second face wall member and one or more side wall members defining a gel compartment for a gel member with a first and second face, wherein at least a section of each one of the first and second face wall member is removable to expose a section of both the first and second face of the gel member essentially corresponding to the separation zone while the gel member is preserved in the cassette.

13 Claims, 24 Drawing Sheets

(56) References Cited

U.S. PATENT DOCUMENTS

| | | |
|---|---|---|
| 4,913,791 A | 4/1990 | Hurd et al. |
| 4,954,236 A | 9/1990 | Kushner et al. |
| 5,228,970 A | 7/1993 | Foley et al. |
| 5,543,023 A | 8/1996 | Lugojan |
| 5,865,974 A | 2/1999 | Cabilly et al. |
| 6,027,628 A | 2/2000 | Yamamura et al. |
| 2004/0079638 A1* | 4/2004 | Rooney .................. C07K 1/26 204/450 |
| 2005/0011762 A1 | 1/2005 | Provonchee |
| 2009/0308751 A1 | 12/2009 | Price et al. |

* cited by examiner

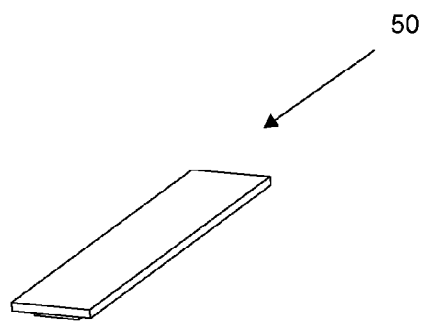
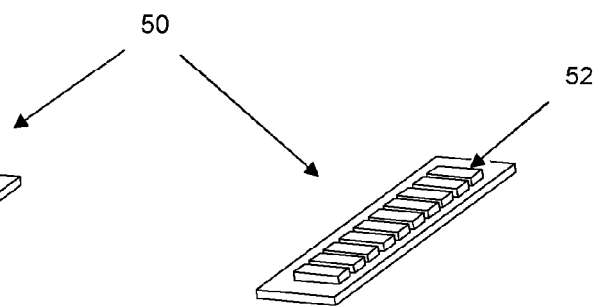
Fig. 2c    Fig. 2d
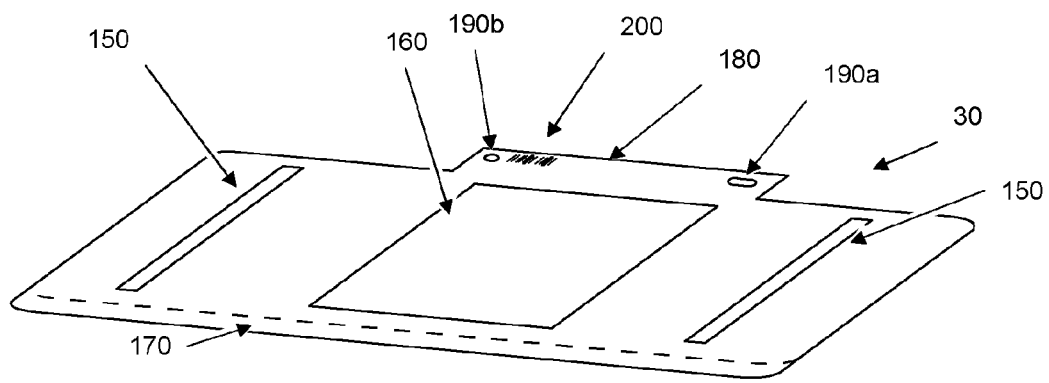
Fig. 2e
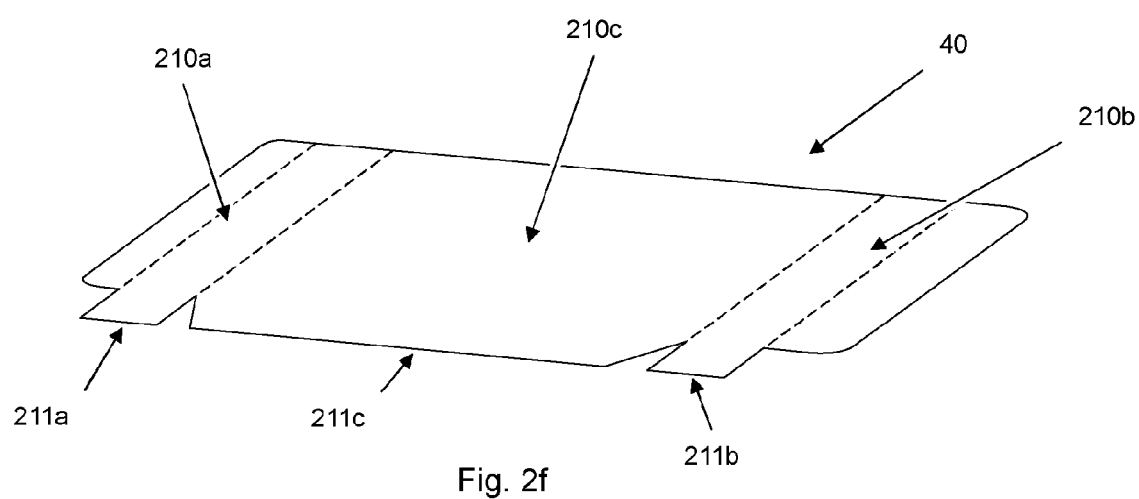
Fig. 2f

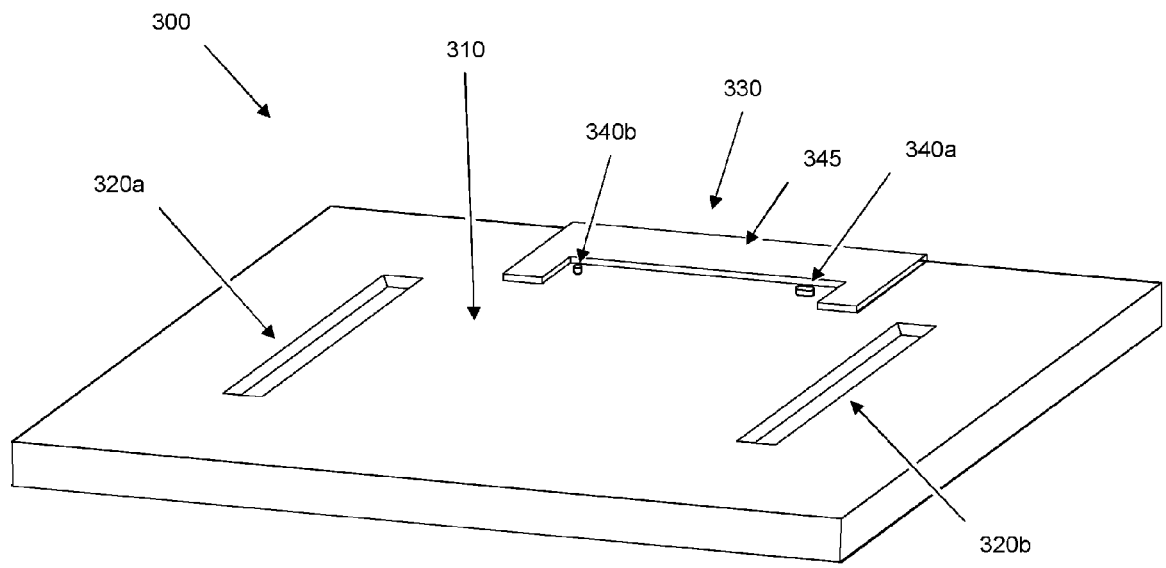
Fig 6
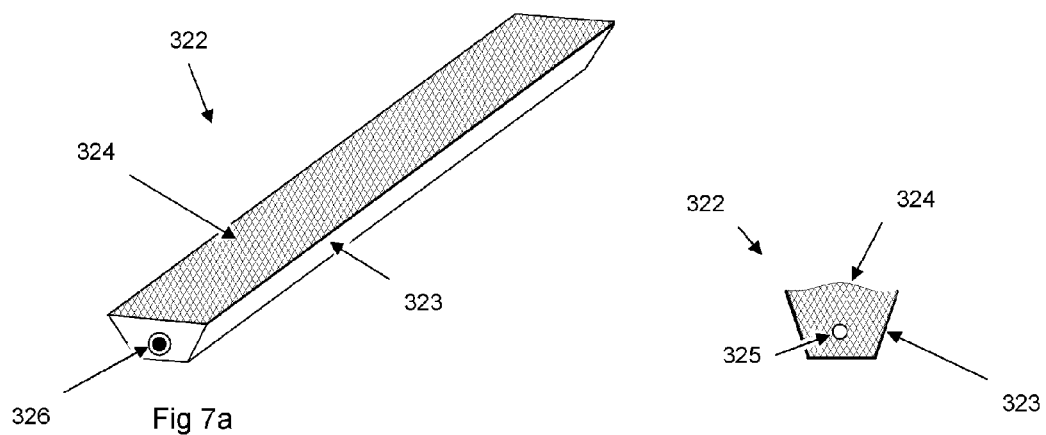
Fig 7a
Fig 7b

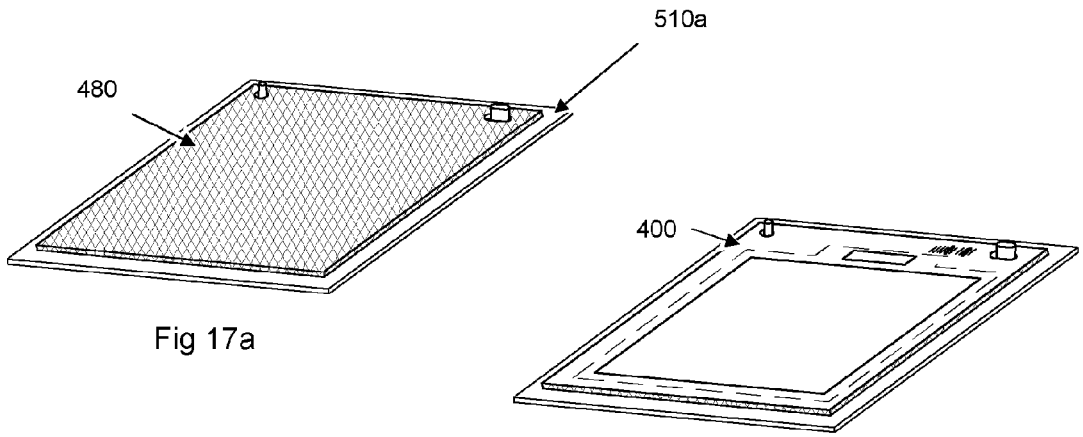
Fig 17a
Fig 17b
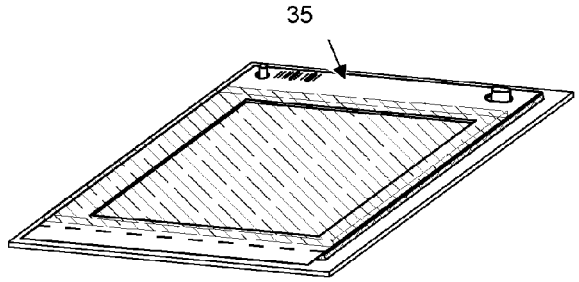
Fig 17c
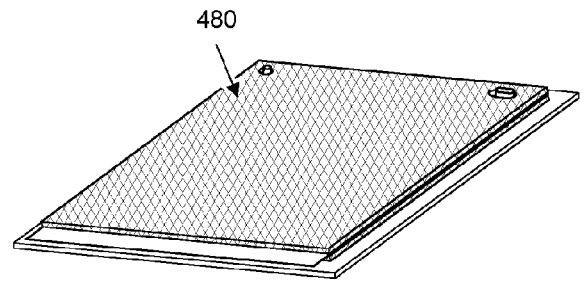
Fig 17d
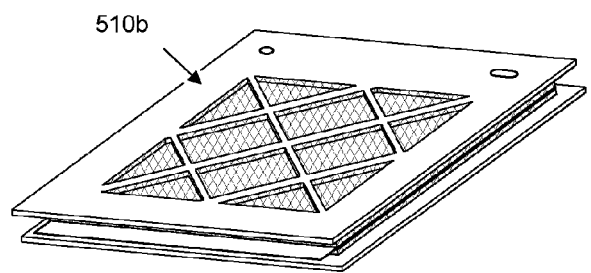
Fig 17e

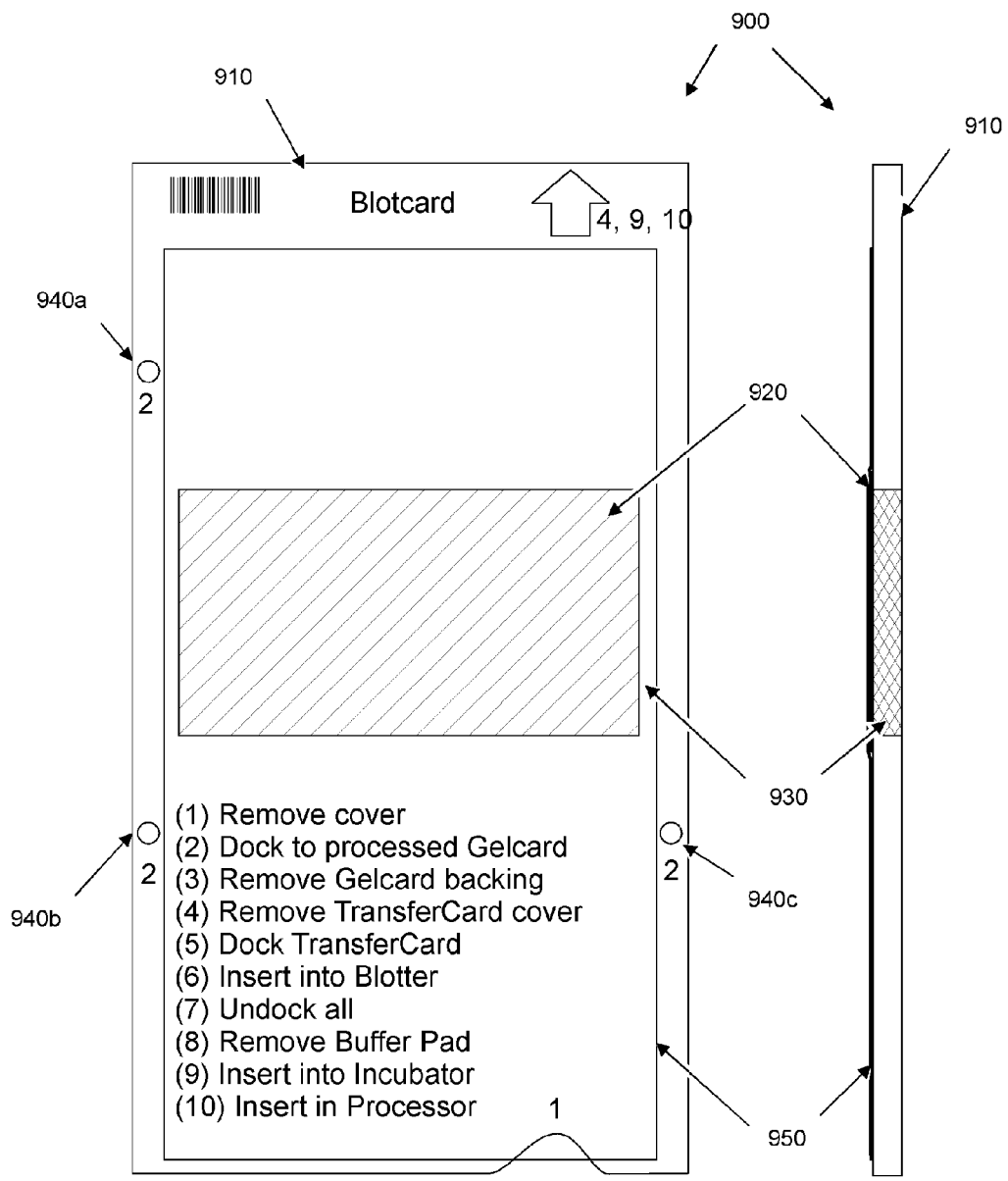
Fig 23c                    Fig 23d

ELECTROPHORESIS GEL CASSETTE

This application is a filing under 35 U.S.C. 371 of international application number PCT/SE2013/050634, filed May 31, 2013, which claims priority to Sweden application number 1250560-8 filed May 31, 2012, in the entire disclosure of which is hereby incorporated by reference.

FIELD OF THE INVENTION

The present invention relates to an electrophoresis gel cassette for electrophoresis experiments, and more particularly to an electrophoresis gel cassette with improved handling.

BACKGROUND OF THE INVENTION

Electrophoresis is a commonly used method for analysis, wherein charged molecules and particles migrate in a separation medium, usually a gel, which is subjected to an electrical field between two electrodes. Separation of proteins may be by isoelectric point (pI), molecular weight, electric charge, or a combination of these factors.

The separation gel is usually placed on a support and two opposing ends of the gel are contacted with an electrode buffer in solution or rigid form. The electrodes may be inserted in vessels containing the electrode buffers. The buffer solutions from both the electrolytic medium and a reservoir for ions to keep the pH and other parameters constant. After separation, the molecules are detected and identified in different manners: e.g. visually by staining the gel or by optical means such as scanning or imaging the stained gel or labeller samples by a laser scanner or the like.

Gel electrophoresis is today routinely used for separating biomolecules such as proteins, peptides, nucleic acids etc. Samples are handled in different types of screening, identifying (cell signaling, expression & purification) or in clinical tests. Protein samples can derivate from e.g. human, mammalian tissue, cell lysates or bacterial, insect or yeast cellular systems. The electrophoretic conditions for different types of molecules are different and have to be adapted in many cases. Thus, both the gel and the buffer solutions must often be chosen for each type of sample.

The preparation of the electrophoresis process includes several rather laborious steps. A suitable gel is chosen and placed or molded on a support. The gel is contacted with the buffer solutions. A common way is to have a gel slab in a cassette of glass or plastic in contact with the buffer solutions in buffer tanks. For each run the gel has to be placed on the support or the cassette be prepared. Then the buffer tanks are filled with buffer solutions and the samples are applied on the gel. To go away from the handling of buffer solutions in buffer tanks it has been suggested, in WO 87/04948, to incorporate the buffer substance in a gel material whereby the buffer is obtained in the form of a buffer strip. In addition U.S. Pat. No. 6,368,481 discloses a precast electrophoresis cassette wherein buffer strips are incorporated as an integral part of the cassette.

Following the electrophoretic separation and in order to detect specific proteins in a given sample, the proteins may be transferred to a membrane (typically nitrocellulose or PVDF), where they are probed (detected) using antibodies specific to the target protein, a process commonly referred to as western blotting or immunoblotting. The primary method for transferring the proteins to the membrane is referred to as electroblotting and uses an electric current to pull proteins from the gel into the membrane. The proteins move from within the gel onto the membrane while maintaining the organization they had within the gel, whereby the proteins are exposed on a thin surface layer for detection. The proteins bind to the surface of the membrane due to its non-specific protein binding properties (i.e. binds all proteins equally well). In order to avoid unspecific binding of probing antibodies, remaining binding sites on the membrane may be blocked.

During the probing (detection) process the membrane is with the transferred proteins are incubated with specific primary antibody directed towards the protein of interest and secondary antibody e.g. for the protein of interest with a modified antibody which is linked to a reporter enzyme; when exposed to an appropriate substrate this enzyme drives a colorimetric reaction and produces a colour or by fluorescently labelled targets (dyes), that may be detected by a suitable imaging technique.

Electrophoresis and the following blotting step is traditionally characterized by a lot of manual handling of both gels and membranes, as well as a range of liquids, e.g. buffers, reagents, wash solutions etc. Some attempts to facilitate and/or automate the workflow have been made in the past, but there are very few U.S. Pat. No. 5,674,006 discloses one example of an apparatus for efficiently circulating and moving a fluid across a workpiece. The apparatus can provide for the automated handling of the fluids used, and is well suited for use in the staining and fixing of biological assays such as electrophoresis gels.

SUMMARY OF THE INVENTION

The object of the invention is to provide a new electrophoresis gel cassette, which electrophoresis gel cassette overcomes one or more drawbacks of the prior art. This is achieved by the electrophoresis gel cassette as defined in the independent claim.

One advantage with the electrophoresis gel cassette is that it provides for facilitated handling of electrophoresis gels as it comprises a rigid support to which the gel is attached.

According to one embodiment there is provided an electrophoresis gel cassette comprising a first and a second face wall member and one or more side wall members defining a gel compartment for a gel member with a first and second face, wherein at least a section of each one of the first and second face wall member is removable to expose a section of both the first and second face of the gel member essentially corresponding to the separation zone while the gel member is preserved in the cassette.

According to one embodiment the side wall members are formed integrally with one of the face wall members forming a cassette body.

According to one embodiment the removable sections of the first and second face wall members are provided with low gel adhesion properties with respect to the gel member.

According to one embodiment at least one of the first and second face wall members is provided with one or more removable sections arranged to expose a buffer contact section of the gel member.

According to one embodiment the electrophoresis gel cassette comprises integrated buffer compartments and optionally electrodes.

According to one embodiment at least one of the removable sections of the first and second face wall members is formed of a plastic film.

According to one embodiment at least one of the removable sections of the first and second face wall members is formed of as a rigid lid.

According to one embodiment at least one of the removable sections of the first and second face wall members is formed of two or more laminated layers of plastic film, wherein the first layer facing the gel compartment has one or more openings formed therein which are covered by one or more pealable sections of the second layer.

According to one embodiment the first layer is comprised of a rigid polymer film with adhesive layers applied to both faces and the second layer is comprised of a rigid polymer film.

According to one embodiment the first layer is comprised of a PET film with adhesive EVA layers applied to both faces and the second layer is comprised of a PET film.

According to one embodiment the electrophoresis gel cassette comprises a precast gel.

According to one embodiment at least one of the first and a second face wall member is comprised of an optically transparent material to allow imaging of the gel without opening the cassette.

According to one embodiment the electrophoresis gel cassette is provided with an alignment structure defining a positional reference for alignment of the gel cassette.

According to one embodiment the electrophoresis gel cassette is provided with an identification code.

A more complete understanding of the present invention, as well as further features and advantages thereof, will be obtained by reference to the following detailed description and drawings.

BRIEF DESCRIPTION OF THE DRAWINGS

FIGS. 2a to 2f show components of the electrophoresis cassette of FIG. 1.

FIG. 6 shows a schematic view of an electrophoresis tray that is compatible with the electrophoresis cassette for running electrophoresis experiments using the same.

FIGS. 7a and 7b shows a schematic view of a buffer pad for use with an electrophoresis tray of FIG. 6.

FIGS. 17a to 17e schematically show the assembly of a transfer sandwich for electroblotting.

FIGS. 23a-23g shows a schematic protein analysis concept according to another schematic embodiment

DETAILED DESCRIPTION OF THE INVENTION

Throughout this disclosure, the separation-zone of an electrophoresis gel is defined as the part of the gel wherein the separated species of the sample are located after a completed electrophoresis run.

Figure 1:
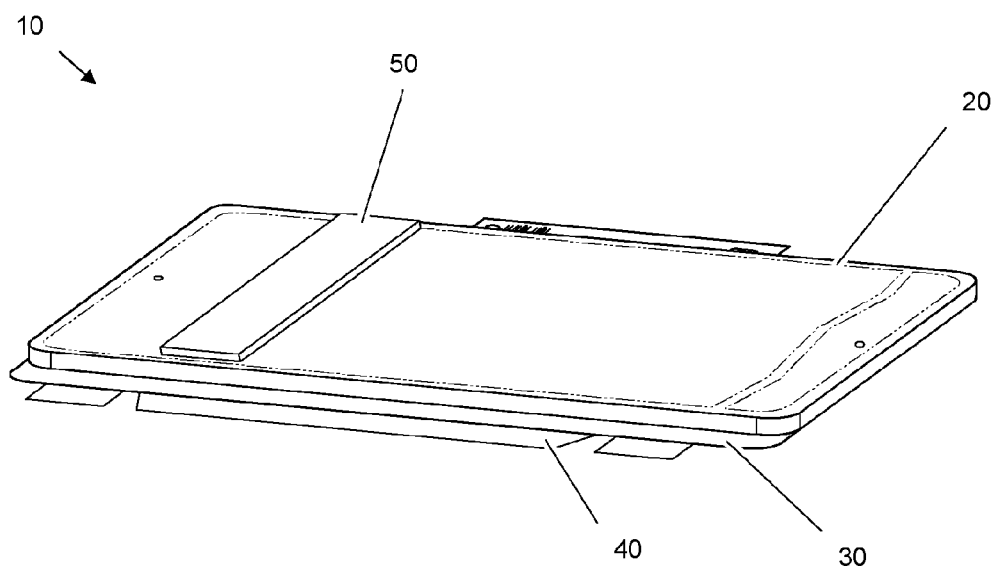
FIG. 1 is a schematic perspective view of an electrophoresis cassette according to one embodiment.

FIG. 1 is a perspective view of an electrophoresis cassette 10 according one schematic embodiment. The cassette 10 comprises a cassette housing 20, a detachable gel support frame 30, a section-wise removable backing film 40 and a removable sample well cover 50. FIG. 1 shows the electrophoresis cassette in assembled state. The gel cassette 10 defines therein a gel compartment for molding a flat gel member 36 for electrophoretic separation. According to one embodiment, the electrophoresis cassette 10 is a precast cassette, but alternatively, the cassette 10 may be empty and ready for molding of a custom gel in the gel compartment, e.g. by the end customer.

Figure 2A:
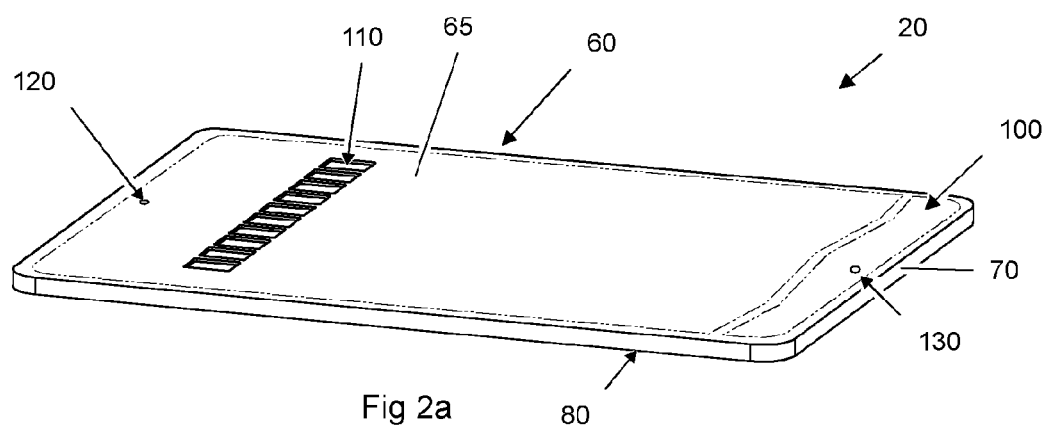
Figure 2B:
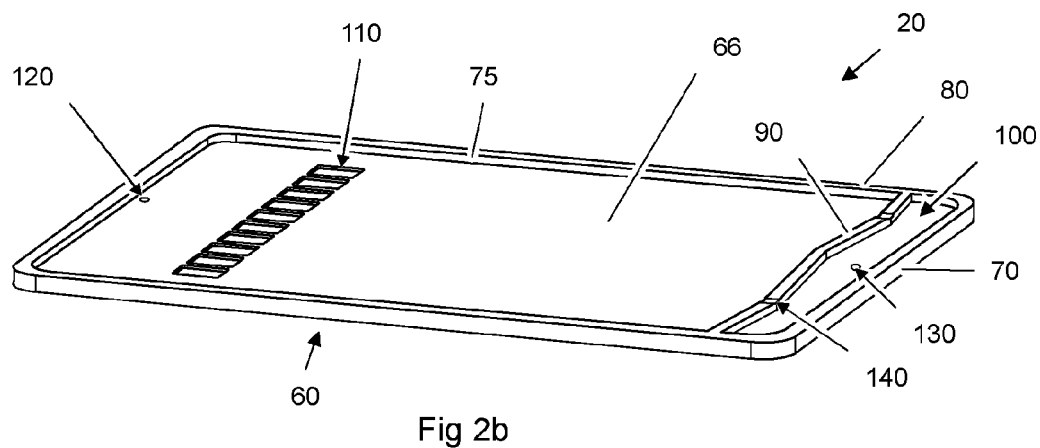

FIGS. 2a and 2b shows the cassette housing 20 with the other components of the cassette 10 removed. FIG. 2a is a top view whereas FIG. 2b shows the cassette housing 20 from below. The cassette housing 20 is generally comprised of a thin upper wall 60 with an upper face 65 and a lower face 66, and a rim 70 that projects downwards from the upper wall 60 around its periphery with a bottom face 80 and an inner wall 75. The lower face 66 of the upper wall 60 and the inner wall 75 of the rim 70 essentially defines the gel compartment, which may be closed from below by attaching the support frame 30 and the removable backing film 40 to the lower face 80 of the rim 70, as is shown in FIG. 1 and will be discussed in more detail below. In the disclosed embodiment, the thickness of a gel member 36 (as schematically disclosed in FIG. 4), molded in the cassette 10 will be essentially the same as the height of the inner wall 75 of the rim. In the disclosed embodiment, the upper wall 60 is of uniform thickness whereby the gel member 36 also will be of uniform thickness, provided that the support frame 30 and the removable backing film 40 are flat as in the disclosed embodiment. The thickness of the gel is preferably adapted to the specific gel type and the buffer system used, as well on the desired currents involved in the electrophoresis step. Further, as is disclosed in more detail below, in alternative embodiments features of the cassette housing 20 may be formed to provide for a gel member 36 of different thickness in different sections thereof.

As the cassette housing 20 should provide a rigid structure to the cassette 10 during storage and use, it should be made of a suitably rigid material. Moreover, as will be disclosed in detail below, the cassette 10 is designed for running electrophoresis separation, therefore the cassette housing 20 should be electrically insulating. In some embodiments, wherein the gel to be molded in the cassette is polymerized by UV radiation, the cassette material may be selected so as to not essentially degrade or get discolored by UV radiation in doses corresponding to polymerization. Moreover the cassette material may be selected so as to not hinder polymerization of the gel, and depending on the design of the cassette 10 the material may be selected so as to exhibit a suitable adhesion to the gel, e.g. low adhesion if the gel member 36 is arranged to be removed from the cassette housing 20, or high adhesion if it is arranged to be retained therein. According to one embodiment, the cassette 10 is further designed to be used in a combined electrophoresis and fluorescence imaging apparatus wherein the gel member 36 may be imaged during or after the electrophoresis step while still in the cassette, as will be disclosed in detail below. Therefore, at least the section of the upper wall 60 covering the separation-zone of the gel member 36 should be sufficiently transparent to electromagnetic radiation of relevant wavelengths. According to one embodiment, the whole cassette housing 20 is injection molded in the same material. Moreover, all components of the cassette 10 may be selected so as to be non/low fluorescent. According to one embodiment, the cassette housing 20 is made of a rigid polymer, such as Cyclo Olefin Polymer (COP), Cyclic Olefin Copolymer (COC), polypropylene (PP), Polyethylene terephthalate (PET), polycarbonate, polymethyl methacrylate (PMMA), combinations, variants thereof or the like.

In the disclosed embodiment there is provided a transverse wall 90 arranged to divide the gel compartment into an electrophoresis compartment and an over-fill chamber 100 arranged to receive excess gel solution during the step of molding the gel member 36. Moreover, there is a fill port 120 at the opposite end of the electrophoresis compartment with respect to the over-fill chamber 100, and an air vent 130 in the over-fill chamber 100. The process of molding a gel in the cassette 20 will be disclosed in more detail below with reference to FIGS. 3a to 3c.

Figure 20A:
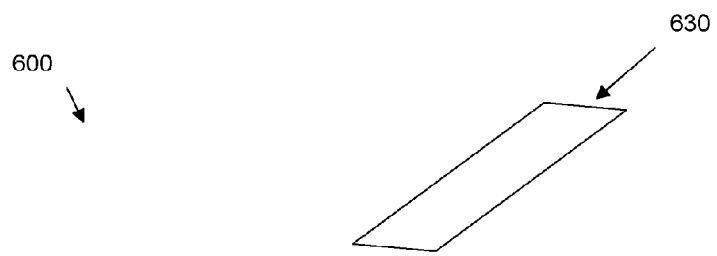
FIGS. 20a-h show another schematic embodiment of an electrophoresis cassette
Figure 20B:
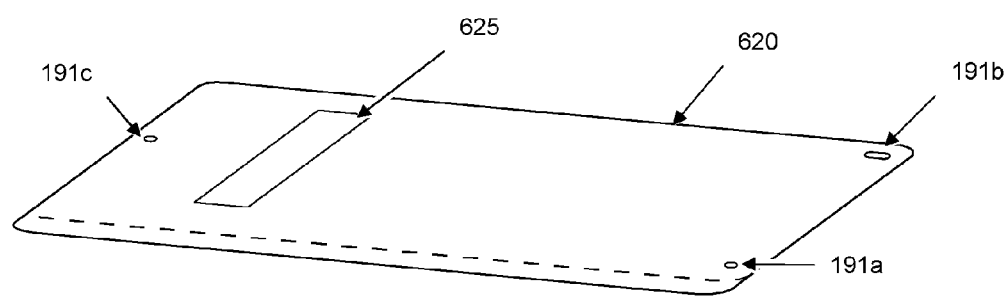
Figure 20C:
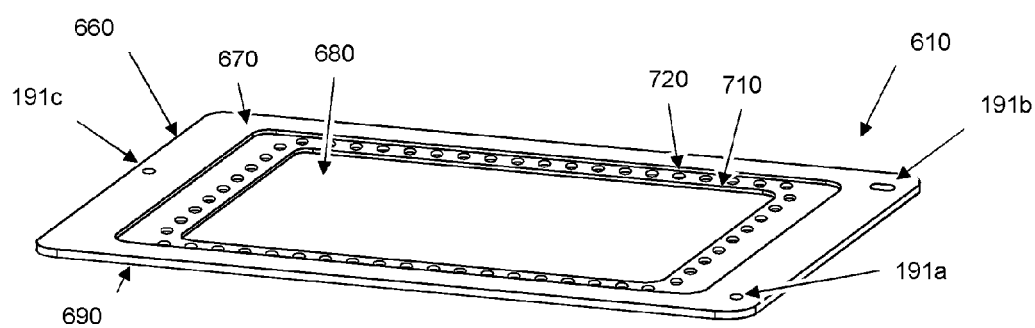
Figure 20D:
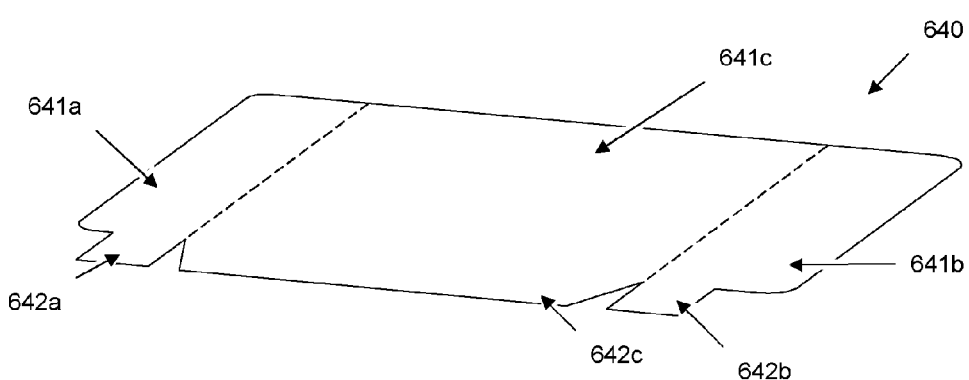
Figure 20E:
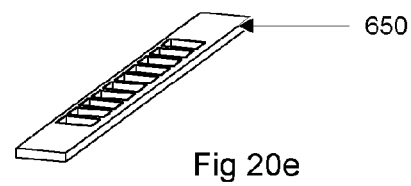

The disclosed cassette 10 is provided with 10 sample well openings 110 for enabling loading of sample onto the gel member 36 for separation, each sample well opening 110 corresponding to one electrophoresis lane during separation. The number and shape of sample well openings 110 may vary depending on the actual dimensions of the electrophoresis cassette, the type of separation and the electrophoresis gel type etc. There may be any suitable number of sample well openings 110 between 1 and e.g. 100. In one embodiment, the cassette is provided with one wide sample loading opening extending essentially across the full width of the gel member, replacing the individual sample well openings. In such an embodiment, the user may e.g form wells directly in the gel using a well-comb or the like, or there may be provided one or more sample loading cups that may be attached to the cassette 10 in contact with the gel member 36 for providing a flexible number of separation lanes, e.g. as is schematically disclosed in FIGS. 20e and 20g and will be disclosed in more detail below In FIG. 1 the sample well openings 110 are covered by a removable sample well cover 50 which is disclosed in more detail in FIGS. 2c and 2d. The sample well cover 50 is arranged to fit over the well openings 110 and to keep them closed during the molding process and storage. Before sample is to be loaded into the sample wells 110, the well cover 50 is removed to open the sample wells 110. In the disclosed embodiment, the well cover 50 comprises well forming protrusions 52 that are formed to fit in a mating relationship in the sample well openings 110 to essentially provide a sealing interaction therewith to avoid leakage of gel solution during molding and air into the cassette during storage. According to one embodiment, the well forming protrusions 52 are designed to extend below the lower face 66 of the upper wall 60 into the gel member 36 to form sample wells extending into the gel member 36 when removed. In another embodiment, the well forming protrusions 52 are designed such that they are flush with the lower face 66 of the upper wall 60 to provide an essentially flat surface of the gel member 36 and wherein sample wells are formed by the sample well openings 110. In one embodiment, the sample well cover 50 is arranged to seal against the upper face 65 of the upper wall 60 or a combination thereof. To facilitate removal while providing sufficiently efficient sealing, the sample well cover 50 is made of a suitable elastic material, such as e.g. ethylene propylene rubber (EPM), ethylene propylene diene monomer rubber (EPDM), Polyacrylic rubber, Fluoroelastomers. etc, and variants and different modifications thereof. In order to achieve efficient production as well as required sealing efficiency, the sample well cover 50 may be co-molded with the cassette housing 20, such that the cassette housing 20 is molded in a first step in a first rigid material where after the sample well cover 50 is molded in a second step in a second, elastic material where the cassette housing partly acts as mold. By proper selection of material characteristics and mold design, e.g. non-permanent adhesion to the rigid material, the co-molded sample well cover 50 can be made selectively removable. In one embodiment, an intermediate material providing for suitable adhesion characteristics, may be provided in between the cassette housing 20 and the sample well cover 50, e.g. a thermoplastic material with low melting temperature or the like.

According to the disclosed embodiment, the detachable gel support frame 30 is detachably attached to the bottom face 80 of the rim 70 and the section-wise removable backing film 40 is in turn attached/laminated to the bottom of the gel support frame 30. The gel support frame 30 and the backing film 40 together provide a lower wall that closes the electrophoresis compartment and the over-fill chamber 100 for molding and storage. As is shown in FIG. 2e, the disclosed embodiment of the gel support frame 30 comprises two buffer buffer-slits 150a and 150b and a separation zone window 160 each covered from below by a respective removable section 210a-c of the backing film 40, shown in FIG. 2f By selecting suitable material combinations and adhesive technology, the backing film may 40 be laminated onto the bottom face of the gel support frame 30 such that the respective sections 210a-c can be removed e.g. by an operator grabbing and pulling a respective peel tab 211a-c. As will be discussed in more detail below, in order to run an electrophoresis experiment, the sections 210a and 210b of the backing film 40 are removed in order to place the gel in contact with respective buffer sources, e.g. buffer pads in an electrophoresis apparatus. Following the electrophoresis run, and in order to provide access to the separation-zone of the gel member 36 for transfer/blotting and probing, the section 210b is removed to uncover the bottom face of a gel member 36 through the separation-zone window 160. In order to allow removal of the sections 210a-c of the backing film 40 without damaging the gel member 36, at least the sections of the film 40 being in direct contact with the gel should have sufficiently low surface adhesion with the same. Low surface adhesion may be achieved by selecting suitable material and surface properties for the whole film and/or modifying the surface properties at the specific interaction-zones, e.g. surface roughness, surface coating, laminating other material to said zones or the like. According to one embodiment, the gel support frame 30 is comprised of a rigid polymer film with adhesive layers applied to both faces thereof and the backing film 40 is comprised of a plain polymer film bonded to the rigid polymer film by the adhesive layer. By this arrangement, the adhesive layer on the housing side of the gel support frame 30 may be arranged to provide a removable but essentially airtight bond to the cassette housing 20, and to provide a high gel adhesion compared to the gel adhesion of the cassette housing 20 and the gel adhesion of the polymer film of the backing film 40. According to one embodiment, the rigid polymer film of the of the gel support frame 30 may be a Polyethylene terephthalate (PET) film with adhesive layers applied to both faces in the form of a melt-adhesive, such as ethylene-vinyl acetate (EVA) or another adhesive with suitable properties for pealable bonding, and the polymer film of the backing film 40 may be a PET film. In this embodiment, the support frame 30 with the adhesive layers only covers parts of the gel member 36 that do not need to be accessible from the bottom thereof and hence has openings which correspond to the respective removable sections of the backing film 40. The support frame 30 has a thin adhesive layer of a material, e.g EVA or another pealable adhesive, which melts at a lower temperature than the PET foil itself and hence the backing film 40 and the support frame 30 can be laminated together using a heat lamination process and finally releasably attached to the cassette housing 20 by a heat bonding process or the like. It has been experimentally verified that an EVA layer meet the crucial property of high gel adhesion for tested gel compositions, without disturbing the gel polymerization or other characteristics which are necessary in this concept.

According to one embodiment, the stack of foils is laminated at approximately 100-115° C. and this procedure should result in a flat, not creased or wrinkled, foil. By using a lower temperature the removable section 210*a-c* of the backing film 40 are more easily opened. The backing film 40 may be thick enough to give a stable feeling, i.e. not too elastic or flimsy, but also thin enough to allow cooling during electrophoresis as will be disclosed in more detail below. According to one embodiment, the backing film 40 may be from e.g. 0.1 to 0.4 mm of thick or any value there between depending on the material of the film. Adhesion to cassette: must be strong enough to prevent leakage but must also allow opening of the foil by hand with little force.

In order to greatly improve handling of the gel member 36 in the steps following the electrophoresis run, the gel support frame 30 is designed to stay attached to the gel member 36 after removal from the cassette 10. The support frame 30 is formed of a suitably rigid material to preserve the shape of the gel and to facilitate handling of the gel member 36 by providing accessible gripping portions that are not covered by the gel member. After removal of the section 210*c* of the backing film 40 the lower face of the separation zone of the gel member 36 is accessible through the separation-zone window 160. In order to achieve proper attachment of the gel member 36 to the support frame 30 it should be designed with high surface adhesion to the gel member. This may be achieved by selecting suitable material properties and/or by surface modification e.g. surface roughness, surface coating or the like as discussed above.

The support frame 30 is attached to the bottom face 80 of the rim 70 such that it is easily detachable, but still provides adequate sealing around the rim 70 to keep the gel compartment sealed during molding and storage. This may e.g. be achieved by selection of suitable material parameters and e.g. use of adhesive, or heat welding. According to one embodiment the cassette housing 20 is made of a rigid polymer and the support frame 30 of a rigid polymer film rigid polymer film with adhesive layers applied to both faces. The support frame 30 is provided with at least one peel tab 170 for pulling the support frame 30 to detach it from the cassette housing 20 together with the gel member. According to one embodiment, the support frame 30 comprises one or more reinforcement layers (not shown) at exposed sections, like peel tabs or the like. In order to secure that the gel member 36 is released from the cassette housing 20, at least the inner walls of the cassette housing 20 should have low surface adhesion with the gel. Low surface adhesion may be achieved by selecting suitable material and surface properties for the whole film and/or modifying the surface properties, e.g. low surface roughness, surface coating, or the like as discussed above.

Moreover, the shape of certain features in the gel compartment may be designed to avoid attachment of the gel thereto to further facilitate release of the gel member, e.g. rounded corners, non-vertical walls and openings etc.

The support frame 30 further comprises an alignment tag 180 with a predefined alignment structure defining a positional reference for alignment of the support frame 30. In the disclosed embodiment, the alignment structure is provided in the form of two alignment holes 190*a* and 190*b*, arranged to ensure that the cassette 10 and/or the support frame 30 is properly aligned with respect to a complementary alignment structure e.g. comprising 2 pins, in an electrophoresis apparatus or the like. Taken that the alignment structure 190*a-b* is provided as a part of the support frame 30 to which the gel member 36 is attached also after the electrophoresis run and in the following transfer step, repeatable positioning of the gel may be achieved which may be very valuable in many situations as will be disclosed in more detail below. Further, the alignment structure may be asymmetrical in a way that it can only be fitted into a complementary alignment structure of an instrument or the like in one unique orientation, whereby, it cannot be inserted in the wrong way, upside down or the like.

Further, the support frame 30 is suitably provided with an identification code 200 or the like which will make it possible to read the identity of the gel member 36 also after it has been removed from the cassette 10 in a secure way. The identification code 200 may e.g. be a machine readable code as a bar-code, matrix-code or the like, and provide the user and/or instruments with relevant information.

In the disclosed embodiment, the gel support frame 30 is comprised of a rigid film of an electrically insulating material, e.g of a polymer material. In this context, the term rigid refers to the film being much more rigid compared to the gel, and especially in the plane to avoid distortion of the gel outline. The film may be quite flexible and bendable in other directions (which is a common characteristic for a film) and it should not be brittle, as it has to be possible to release the gel member 36 from the cassette housing by pulling the peal tab 170 of the support frame 30. It may in fact be beneficial for the current design that the support frame 30 is flexible in the out of plane direction as it then will facilitate removal of the gel member 36, by applying the release force mainly along the extension of the film to gradually release the gel from the cassette housing 20. In other embodiments, as is schematically disclosed in more detail below, the support frame 30 may be of a more frame-like rigid structure, defining a substantial part of the gel compartment and the upper and lower walls 60 and 40 being removable from the rim of the rim 70 of the frame-like rigid structure.

Figures 3A, 3B, 3C:
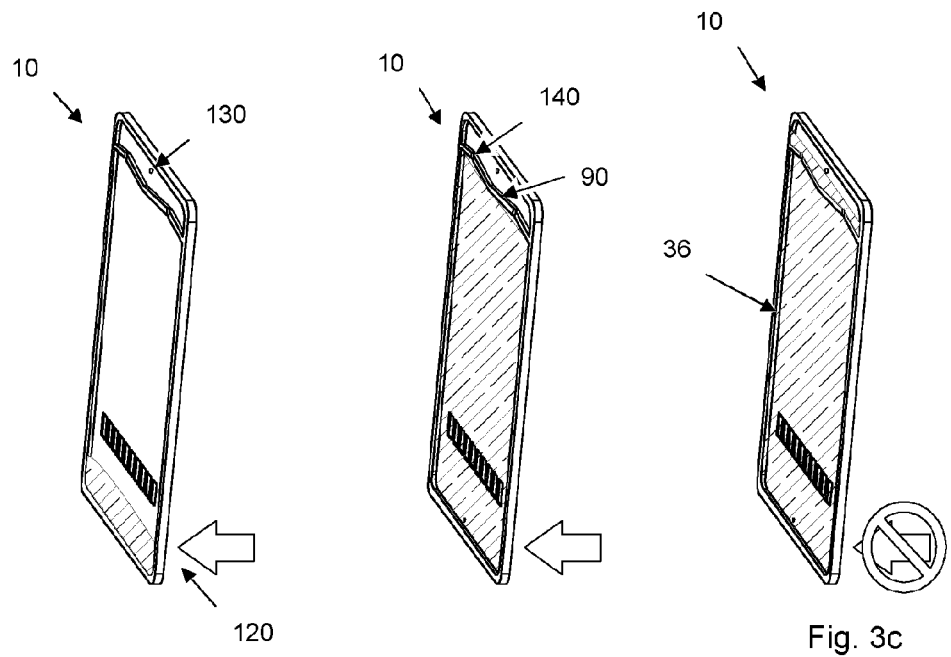
FIGS. 3a to 3c schematically show a process for filling the electrophoresis cassette of FIG. 1.

FIGS. 3*a* to 3*c* schematically show a sequence of filling a cassette 10 with gel solution 210 to mold a gel member. In FIGS. 3*a* to 3*c* the support frame 30 and the removable backing film 40 are not shown for illustrative purposes. As is indicated in the figs, the cassette 10 is designed to be filled with gel solution from the bottom up in an upraised position. According to one embodiment, the cassette 10 is arranged in a support fixture (not shown) arranged to support the relatively thin upper and lower walls of the gel compartment during the molding process until the gel member 36 has been cured in order to ensure uniform thickness of the gel and that no leakage occurs. A suitable fill nozzle (not shown) is connected to the fill port at the lower end of the cassette 10 when placed in an upraised position, and gel solution is pushed into the gel compartment and starts to fill the same from below. As the inlet from the fill port is arranged essentially at the lowermost position in the gel compartment, gel solution can be filled without trapping air bubbles. In FIG. 3b the gel solution front is just about to reach the transverse wall 90 of the over-fill chamber 100. As is best seen in FIG. 2b, the transverse wall 90 is essentially "W"-shaped and tapered towards the over-fill ports 140 at its uppermost positions with respect to the fill direction with one or more intermediate ridge defining separate tapered sections for each over-fill port 140. By means of the shape of the transverse wall 90, air is effectively evacuated from the electrophoresis compartment through the over fill ports 140 before the gel solution front reaches the over fill ports 140. In functional terms, improved air evacuation is achieved, by dividing the gel solution front into two or more segments depending on the width of the cassette, each segment having an over flow port at the upper most position. Moreover, by selecting an appropriate shape and cross-sectional area for the over-fill ports 140, there may be provided a distinct flow restriction for gel solution compared to evacuation of air, whereby the gel solution flow rate in a segment will be reduced as the gel solution front has reached one over-fill port 140 and the flow rate will increase in other segments to even out any unbalance in the flow front position between segments. According to the disclosed embodiment, the over-fill ports 140 are formed by a recess in the transverse wall 90 which is enclosed from below by the support frame 30 to form a narrow port of predefined cross-section. In other embodiments, the over-fill ports 140 may be formed by molded through holes in the transverse wall 90. The fill operation may be stopped when the gel solution has reached the over fill chamber 100 through the over fill ports 140, e.g. by filling a fixed volume in each cassette 10 selected to exceed the volume of the electrophoresis compartment by a predefined amount, or by one or more flow front detectors arranged to detect a flow front at a predefined position with respect to the over-fill chamber, or the like. According to one embodiment, the filling is stopped when a fill pressure detector (not shown) detects an increased fill pressure resulting from gel solution entering the over-fill chamber through each over-fill port According to one embodiment, the distal section of the gel compartment formed by the transverse wall 90 is tapered over its whole width towards one over-fill port 140 (not shown). In other embodiments, as e.g. is shown in some of the following embodiments, there is no transverse wall 90 and the air removal during gel filling is handled by alternative means.

Figure 4:
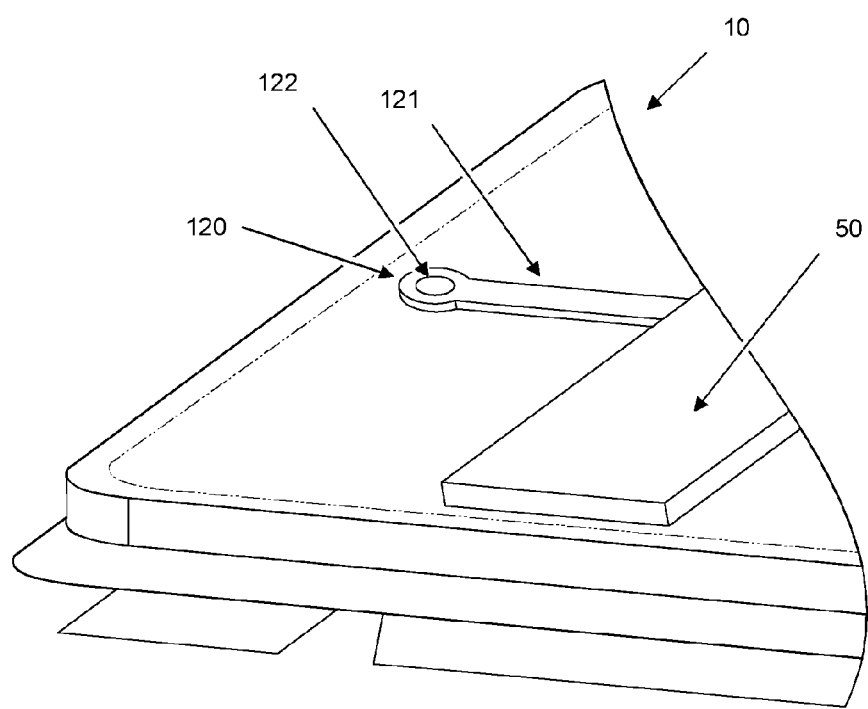
FIG. 4 shows an enlarged section of the lower end of the cassette according to one embodiment.

FIG. 4 shows an enlarged section of the lower end of the cassette 10 according to one embodiment, wherein the fill port 120 comprises a membrane section 122, e.g. a septa, arranged to allow penetration of a fill nozzle, e.g. in the form of a syringe needle or the like, thereto for feeding gel solution into the cassette 10, but which effectively prevents the injected solution from leaking out when the fill nozzle has been removed and air from entering into the gel compartment. In the disclosed embodiment, the fill port 120 and the membrane section is comprised of an elastic material. According to one embodiment, the fill port 120 may be co-molded in the same step as the sample well cover 50, with the main difference that the fill port 120 is designed to be permanently attached to the cassette housing 20 whereas the sample well cover is pealable. As the two structures are made of the same material, the fill port 120 may be formed to be retained on the cassette housing 20 by mechanical means, such as by undercutting the opening into which the port 120 is molded, or alternatively by modifying the surface of the cassette housing 20 to increase adheasion. In one embodiment, the fill port 120 and the sample well cover 50 may be molded using the same injection port, and the structures being linked by a resin flow channel leaving a connection member 121 there between. The connection member may e.g. be formed to break upon removal of the sample well cover 50 or may be cut before removal of the sample well cover 50.

Figure 5:
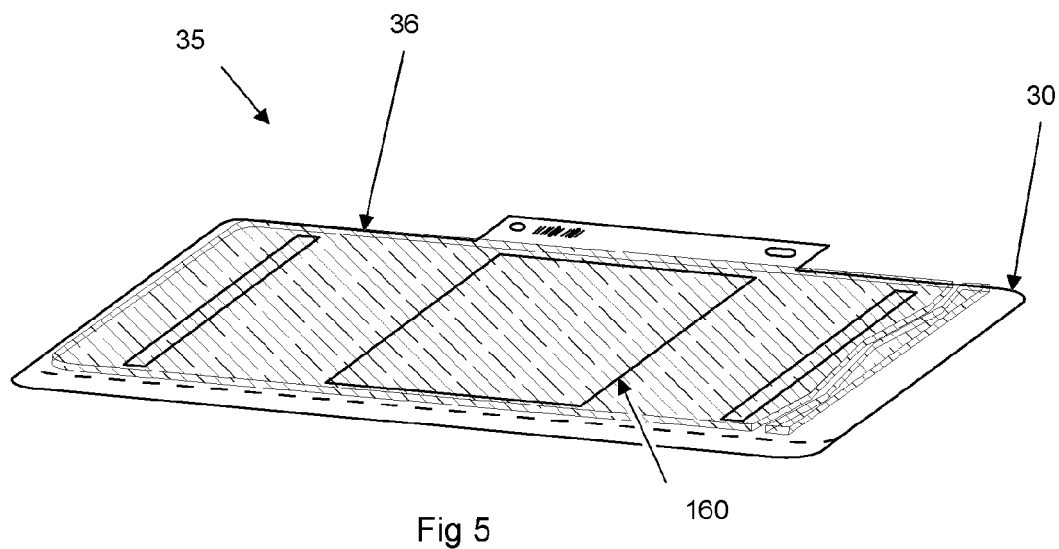
FIG. 5 shows an electrophoresis gel unit with a gel member attached to the top face of a support frame.

FIG. 5 shows an electrophoresis gel unit 35, e.g. formed by the support frame 30 with the gel member 36 attached to the top face thereof, detached from the cassette housing 20. The thus formed gel member 36 is an essentially flat member with an upper and a lower face and a sample separation zone as previously defined. The support frame 30 is arranged to preserve the shape of and to facilitate handling of the gel member 36, while at the same time being formed to allow access to a section of both the upper and lower face of the gel member essentially corresponding to the separation zone. As will be shown below, the accessible section of the section gel member 36 at either face may be larger than the separation zone, but in order to allow proper transfer of separated sample from the gel member 36 to e.g. a blot membrane, by immunoblotting, the accessible section at either face should not be smaller.

Figure 8A:
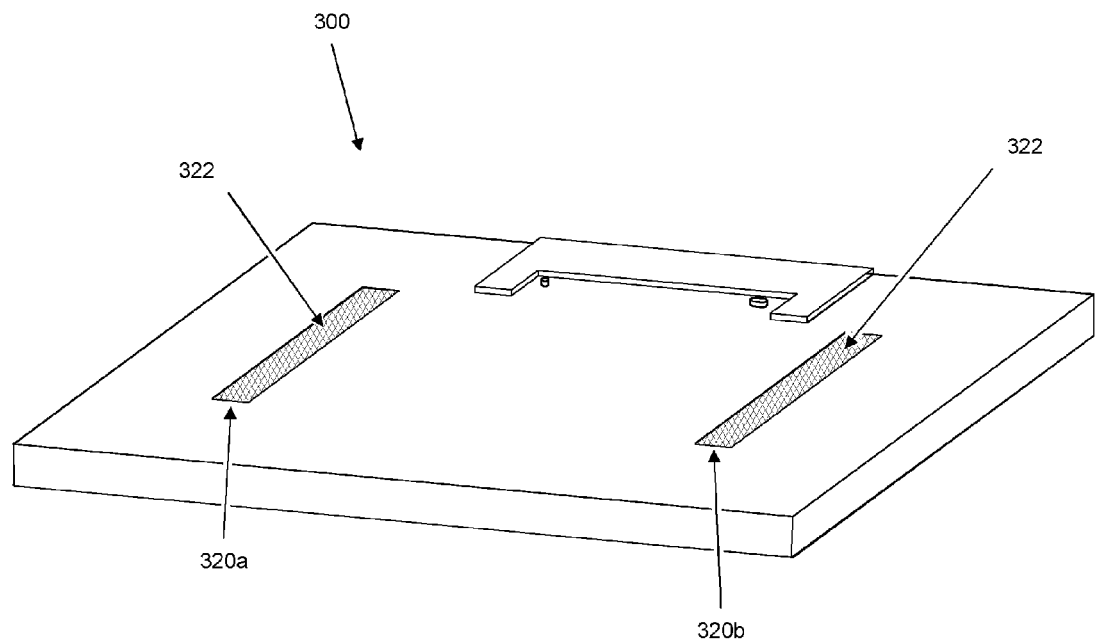
FIGS. 8a to 8c shows a schematic view of the interaction between the electrophoresis tray, the buffer pads and a electrophoresis cassette.

FIG. 6 shows a schematic view of an electrophoresis tray 300 that is compatible with the electrophoresis cassette 10 for running electrophoresis experiments using the same. In FIG. 6 the tray 300 is disclosed as a separate feature, but it may conveniently be an integral part of an electrophoresis apparatus, and it may be comprised of several components and may comprise two or more cassette positions for running two or more electrophoresis experiments in parallel. The tray 300 comprises a cassette support surface 310 for supporting at least the separation zone of an electrophoresis cassette 10 during electrophoresis. The cassette support surface 310 is flanked by a pair of buffer pad holders 320a and 320b respectively, each one arranged to hold a buffer pad 322 (e.g. as is shown in FIGS. 7a and 7b) in a mating position with respect to the buffer connection sections at the back face of the electrophoresis cassette 10. According to one embodiment, the tray 300 comprises a heat transfer unit (not shown) connected to the cassette support surface 310 to control the temperature the electrophoresis cassette 10 during electrophoresis by heat transfer contact with a section of the back surface of the electrophoresis cassette 10. In the disclosed embodiment, the tray 300 comprises a flat top surface with two buffer pad holders 320a and 320b formed as two separate recesses therein, and an alignment structure 330 that is formed to be complementary to the alignment tag 180 of the support frame 30 to ensure proper orientation of the cassette 10 on the tray. In the disclose embodiment, the alignment structure 330 is comprised of an elongated pin 340a, a circular pin 340b and an optional wall member 345. By making the pins 340a and 340b of different cross-sectional shape, the alignment structure is made asymmetric, whereby proper orientation of the alignment tag 180 and the cassette 10 is ensured. When the cassette 10 is properly positioned on the tray 300, the buffer slits 150a and 150b of the support frame 30 are positioned at the respective buffer compartments 320a and 320b to enable mating contact between the gel exposed through the buffer slits 150a and 150b (with the respective removable section 210a and 210b of the backing film 40 removed) and a buffer pad 322, schematically shown in FIGS. 7a and 7b, placed in the respective buffer pad holders 320a and 320b, as is schematically shown in FIGS. 8a, 8b and 8c.

According to one embodiment, the buffer pad 322, schematically disclosed in FIGS. 7a and 7b comprises a cup 323 housing a buffer strip 324 and an electrode arrangement 325. FIG. 7b shows a cross sectional view of FIG. 7a. The cup further comprises an external electrical connector 326 for connecting the electrode arrangement 325 to a power source of the electrophoresis apparatus. Consequently, the tray 300 is provided with complementary electrical connectors (not shown). The cup 323 is formed to fit into the buffer pad holders 320a and 320b so that the top portion of the buffer strip 324 can be placed in contact with the gel in a cassette placed on the tray 300. The buffer strip 324 may be comprised of a buffer substance incorporated in a gel material e.g. the type disclosed in WO 87/04948. By placing the buffer strip 324 in a cup 323, changing the buffer media between electrophoresis runs is greatly facilitated, e.g. compared to placing gel strips directly in the buffer recess. As is disclosed in FIG. 7b, the gel strip 324 may be formed with a raised section to facilitate contact to the gel in the cassette 10.

According to one embodiment, the buffer pad 322 is formed as a disposable unit potentially packed together with the cassette 10, but in another embodiment, the cup 323 including the electrode 325 are intended for reuse with disposable buffer strips 324 that are replaced after use. According to one embodiment, the buffer pads are integrated with the electrophoresis cassette like in U.S. Pat. No. 6,368,481, which is incorporated herein by reference.

Figure 8B:
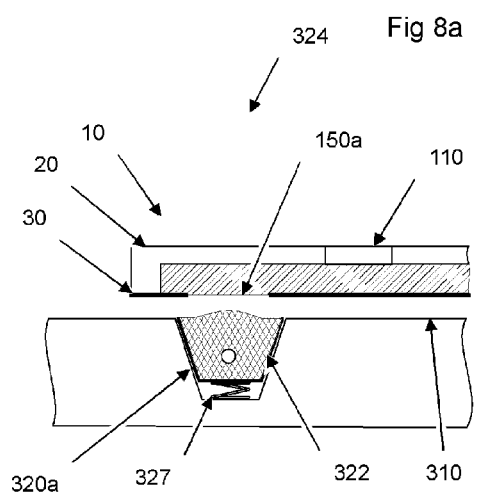
Figure 8C:
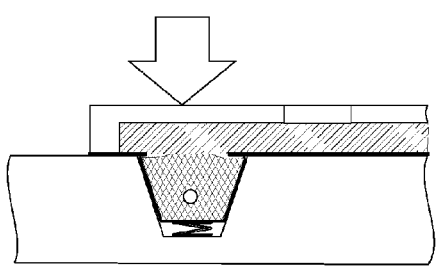

FIGS. 8b and 8c shows a schematic side view of a tray 300 and a buffer pad holder 320a with a buffer pad 322 placed therein and with an electrophoresis cassette 10 elevated slightly above the cassette support surface 310 of the tray 300 in position to be docked onto the tray 300. In order to ensure proper mating contact between the buffer pads and the buffer connection sections at the back face of the electrophoresis the mating of the buffer pads and the buffer connection sections may be biased to some degree. This may be especially important for some gel/pad compositions wherein one may get mass transfer of e.g. water from the pad into the gel, whereby the buffer pad 322 will shrink. By biasing the buffer pad 322 against the gel such situations may be accomplished for. By selecting suitable material properties for the gel component of the buffer pads 322, they may be comprised of a suitable resilient material capable of at least partially providing the biased mating. In one embodiment, the biased mating may be achieved by providing buffer strips of specific shape that allow a certain degree of compression due to its shape. In the embodiment disclosed in FIGS. 8b and 8c a spring element 327 is introduced in the buffer pad holder 320a to provide for the biased mating in combination with the material characteristics of the buffer strip and the shape of the same as is disclosed in FIG. 8c.

In alternative embodiments, the buffer pads 322 may be replaced by buffer strips that are placed directly into the buffer pad holders 320a and 320b and wherein the electrode arrangement 325 is arranged separately in the pad holders. In still alternative embodiments not shown, the buffer pads 322 may e.g. be formed by a container filled with a liquid buffer and comprising an electrode arrangement and a wicking member or the like for establishing contact with the gel member 36.

FIGS. 8 to 11 schematically show the steps involved performing an electrophoresis separation experiment using an electrophoresis cassette 10 and a compatible electrophoresis apparatus 350. The individual order of some steps may vary.

Buffer pads 322 are placed in buffer pad holders 320a and 320b in the tray 300. (FIG. 8).

Removable sections 210a and 210b of the backing film 40 are removed from the cassette 10 by pulling peal tabs 211a and 211b respectively, whereby the gel member 36 becomes exposed through the buffer slits 150a and 150b of the support frame 30 respectively. (FIG. 9)

Figure 9:
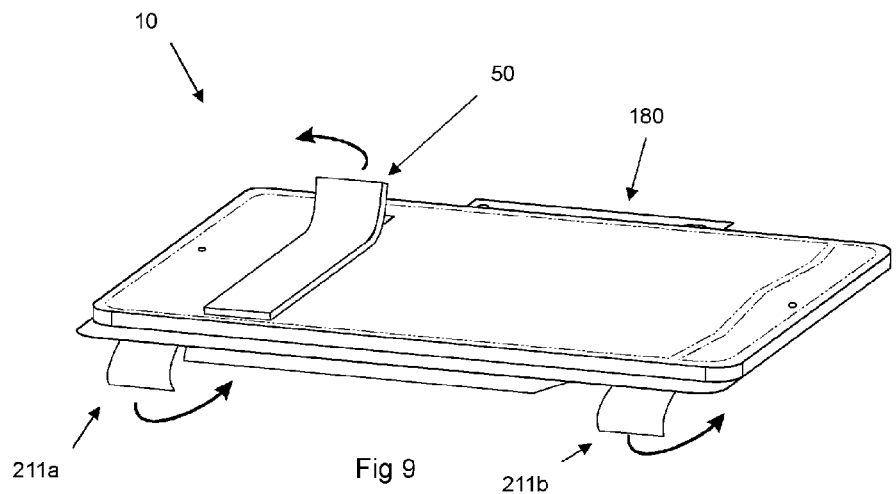
FIGS. 9 to 11 schematically show the steps involved performing an electrophoresis separation experiment using an electrophoresis cassette and a compatible electrophoresis apparatus.

The sample well cover 50 is removed to expose the sample wells 110 (FIG. 9)

Figure 10:
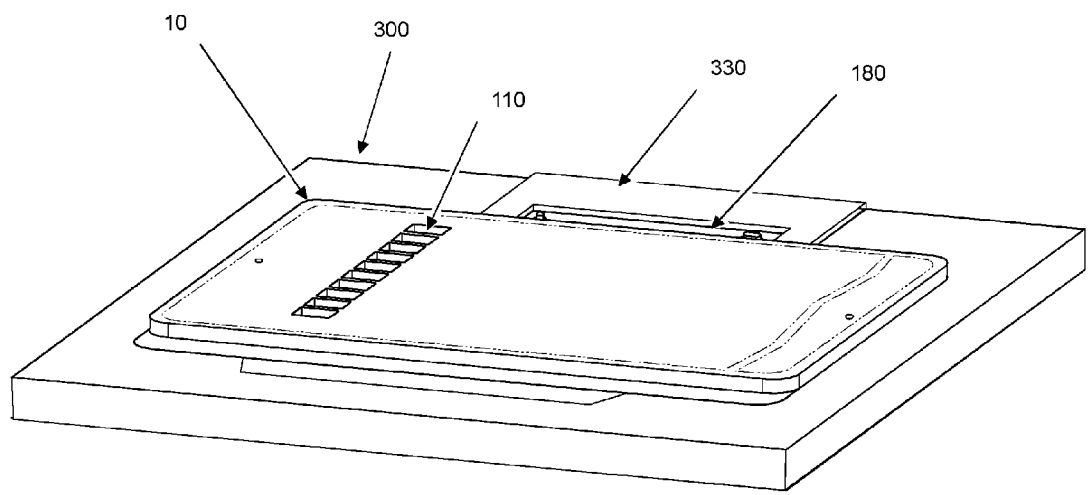

The cassette 10 is positioned on the tray 300 with the alignment tag 180 of the support frame 30 positioned in the complementary alignment structure 330 so that proper orientation of the cassette 10 on the tray 300 is ensured. (FIG. 10)

Sample is loaded into the sample wells 110, e.g. by a pipette 360 or the like. (FIG. 11)

The electrophoresis process is performed using an electrophoresis apparatus 350. (FIG. 11).

Figure 11:
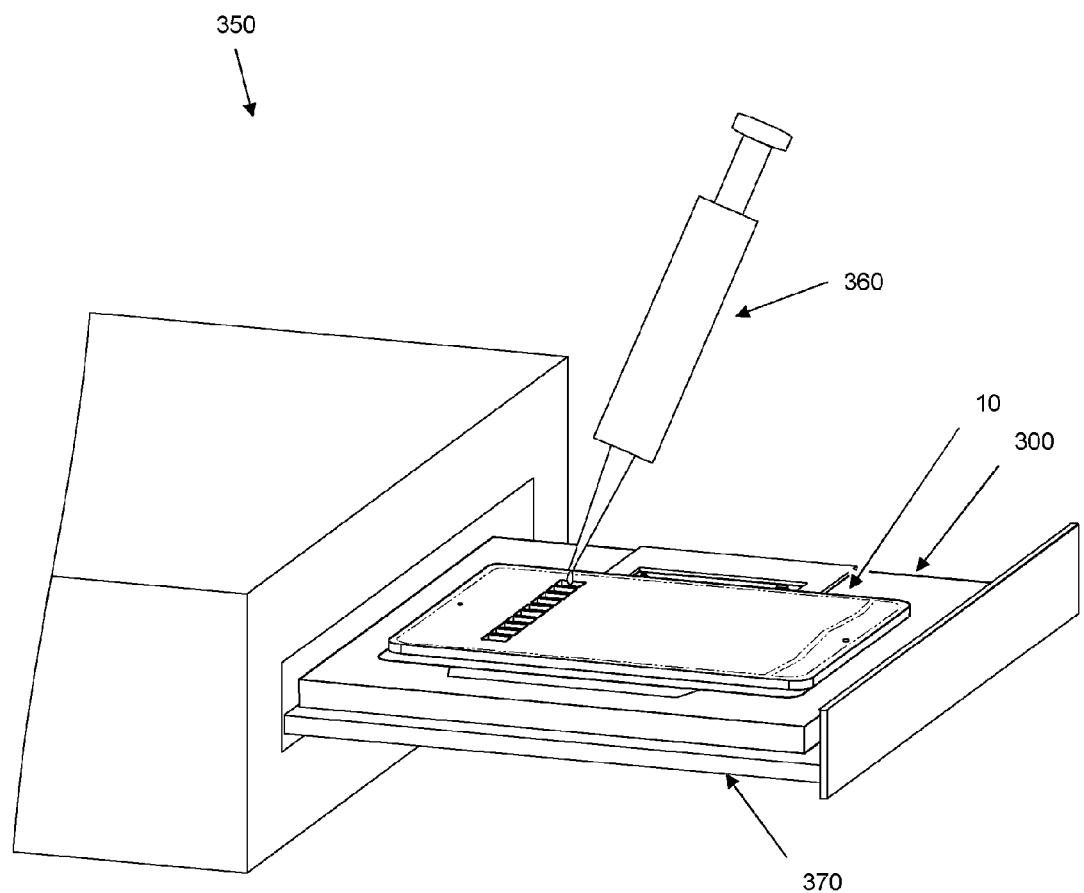

In FIG. 11, the schematically disclosed electrophoresis apparatus 350 is provided with a tray loading mechanism 370 carrying the electrophoresis tray 300. According to one embodiment, the electrophoresis apparatus 350 comprises a fluorescence imaging unit (not shown) for imaging the result of the separation directly in the apparatus. In this way the electrophoresis cassette 10 need not to be moved to a separate imaging unit following the separation. As mentioned above, the disclosed cassette may be designed for imaging, by proper materials selection and design to avoid undesirable optical effects such as fluorescence emitted by parts of the cassette, image distortion etc. One benefit with the disclosed embodiment of the cassette 10, and electrophoresis tray 300 with buffer pads 322 recessed in the tray is that the resulting electrophoresis set up is of low profile, whereby the imaging unit may operate in the close vicinity of the gel to increase sensitivity and resolution, and to avoid negative optical effects. In the disclosed embodiment, the electrophoresis tray 300 is shown in essentially horizontal position with the gel cassette 10 arranged on top thereof. However it should be noted that the electrophoresis tray 300 as well as the gel cassette 10 may be arranged for use in other orientations such as vertical or even upside down.

Figure 12A:
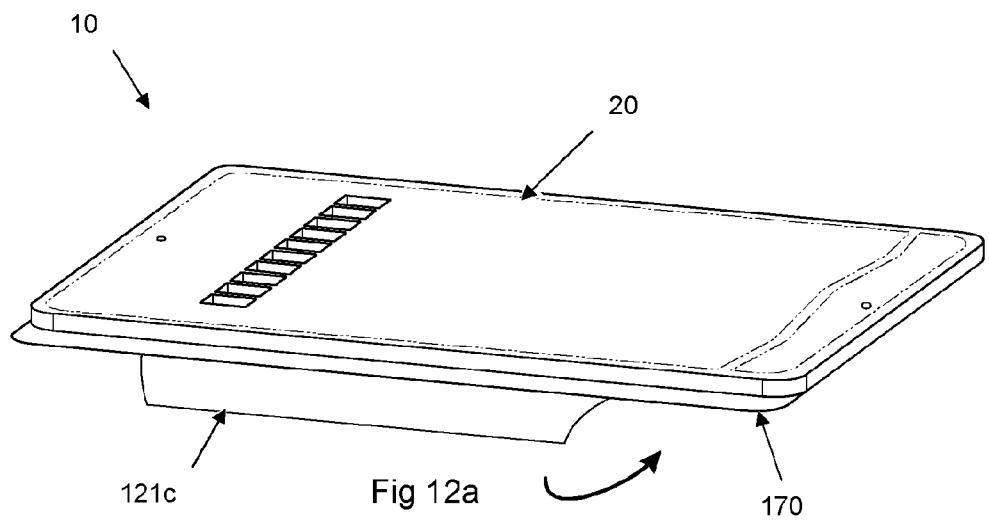
FIGS. 12a to 12c schematically show the steps of removing a gel member attached to the support frame from the cassette housing.
Figure 12B:
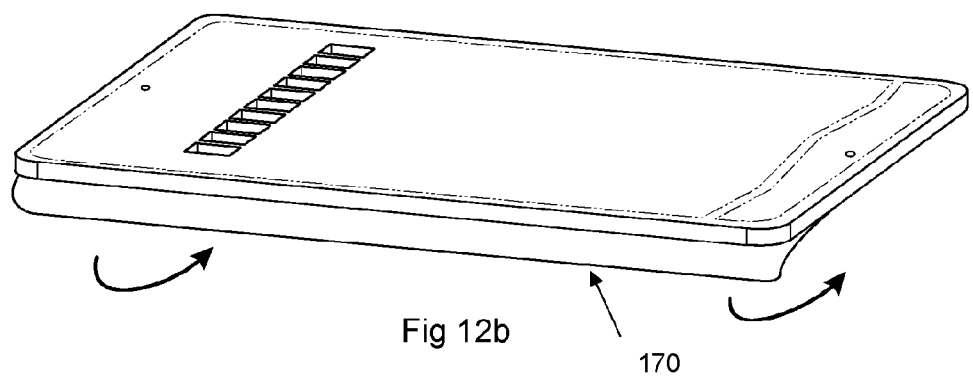
Figure 12C:
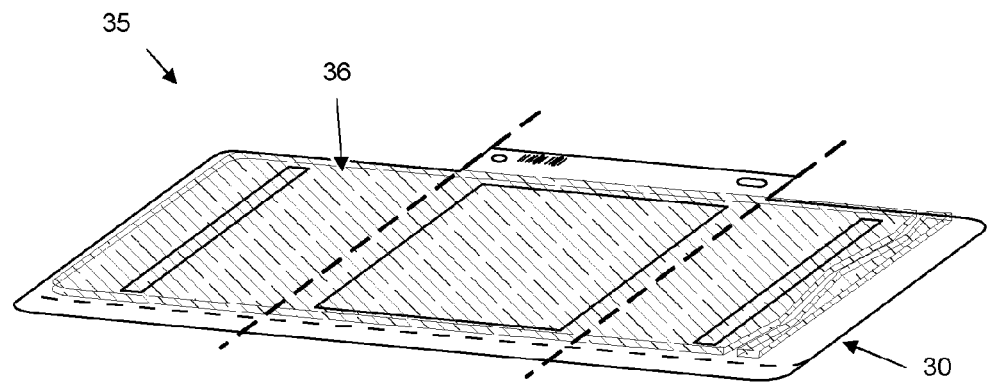

FIGS. 12a to 12c schematically show the steps of removing the gel member 36 attached to the support frame 30 from the cassette housing 20.

Removable section 210c of the backing film 40 is removed from the cassette 10 by pulling peal tab 211c, whereby the separation-zone of the gel member 36 becomes exposed through the separation-zone window 160 of the support frame 30. (FIG. 12a)

Detaching the support frame 30 together with the attached gel member 36 by pulling the peel tab 170. (FIG. 12b)

Figure 13:
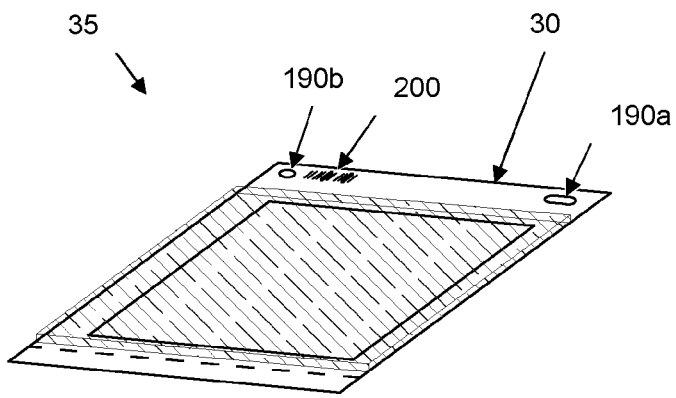
FIG. 13 shows an example of the electrophoresis gel unit

FIG. 12c shows the electrophoresis gel unit 35 comprised of the support frame 30 together with the attached gel member 36 after it has been detached from the housing 20. Depending on the physical format of the cassette 10 and the format requirements due to equipment for the following process steps of e.g. immunoblotting or the like, sections of the support frame 30 and the gel member 36 that are not used in the following steps, may optionally be cut off as is indicated by the dashed lines in FIG. 12c, e.g. leaving a smaller sized support frame 30 with the separation zone of the gel member 36 attached thereto. In order to preserve the benefit of the support frame it should be noted that a sufficient portion of the support frame should remain around the separation-zone window. FIG. 13 shows an example of the electrophoresis gel unit 35 where end sections of the support frame 30 and the gel member 36 have been removed in order to be adapted to the immunoblotting format schematically disclosed in FIGS. 14 to 17e.

Figure 14:
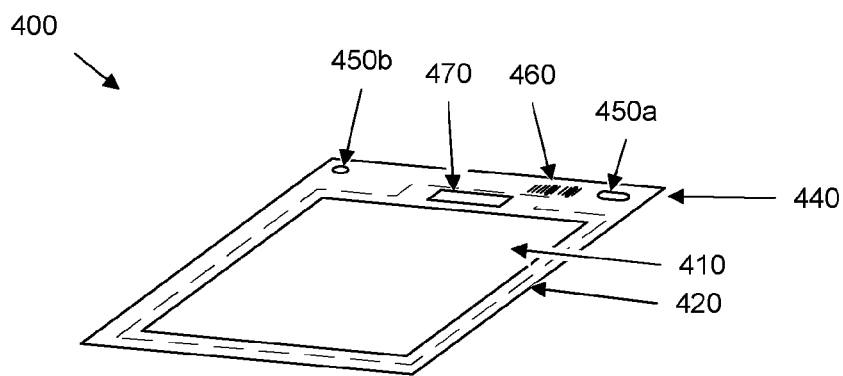
FIG. 14 shows a membrane unit for immunoblotting

FIG. 14 shows a membrane unit 400 for immunoblotting comprised of a membrane 410 that is attached to a rigid blot frame 420. Like for the gel member, in order to greatly improve handling of the membrane unit 400 in the steps of the immunoblotting process, the rigid blot frame 420 is designed to stay attached to the membrane 410 throughout the process steps. The rigid blot frame 420 is formed of a suitably rigid material to preserve the shape of the membrane 410 and to facilitate handling of the membrane 410 by providing accessible gripping portions outside of the transfer-zone. Just as the support frame 30, the rigid blot frame 420 further comprises an alignment tag 440 with a predefined alignment structure in the form of two alignment holes 450a and 450b, arranged to ensure that the membrane unit 400 is properly aligned with respect to a complementary alignment structure e.g. comprising 2 pins, in an transfer unit, a scanner or the like. According to the disclosed embodiment, the alignment structure 450a and b is compatible with or essentially identical with the alignment structure 190a and b of the gel support frame. By means of suitable alignment means the gel member 36 and the membrane unit 400 may be aligned during the transfer process to create a known geometrical relationship between the bands of the electrophoresis gel and the transferred bands. The known geometrical relationship may thereafter be used to correlate evaluation of images of respective gel and membrane unit 400 e.g. to identify lanes from the electrophoresis gel in the image of the membrane unit 400. Further, like the gel support frame 30, the alignment structure 450a-b of the membrane unit 400 may be asymmetrical in a way that it can only be fitted into a complementary alignment structure of an instrument or the like in one single way, whereby, it cannot be inserted in the wrong way, upside down or the like.

Further, the rigid blot frame 420 is suitably provided with an identification code 460 or the like which will make it possible to read the identity of the membrane unit 400. The identification code 460 may e.g. be a machine readable code as a bar-code, matrix-code or the like, and provide the user and/or instruments with relevant information. According to one embodiment, at least one of the support frame 30 and the rigid blot frame 420 is made of a transparent material or is provided with a window arranged to expose the identification code (200 or 460) of the other frame when placed in an aligned position on top of the other, whereby both identification codes may be read in the same operation creating a unique link between a specific gel member 36 and membrane unit 400.

In the disclosed embodiment, the rigid blot frame 420 may be comprised of a rigid film, e.g of a polymer material. In this context, the term rigid refers to the film being more rigid compared to the membrane, and especially in the plane to avoid distortion of the membrane outline. The membrane 410 may be attached to the rigid blot frame 420 in any suitable way that provides adequate bond characteristics. According to one embodiment membrane 410 may be formed of two or more laminated layers of plastic film, wherein one or more sections of the blot membrane is interlaminated in between the layers of plastic film. One or more of the plastic layers may comprised of a rigid polymer film with an adhesive layer applied to one face, and the rigid polymer film may e.g. be comprised of PET and the adhesive layer may e.g. be an EVA layer.

As is schematically disclosed in FIG. 14, the membrane 410 may have an outline, indicated by the dashed line, formed to cover a smaller window 470 in the rigid blot frame 420 which may be used for making manual notes using a pen or the like. As will be disclosed in more detail below, in other embodiments, the rigid blot frame 420 may be of a more frame-like rigid structure, that may be formed to allow positioning of the membrane 410 in contact with a gel member 36 of a complementary electrophoresis gel unit 35.

Figure 15:
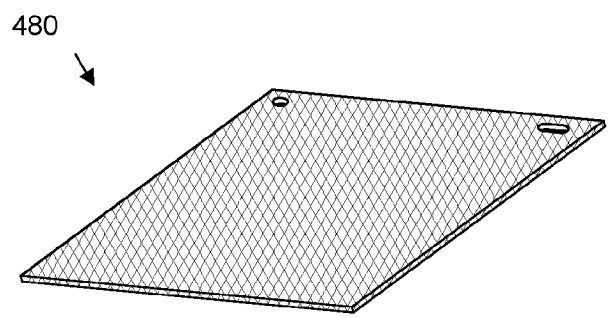
FIG. 15 shows a sponge member to be used in building a transfer sandwich for electroblotting.

FIG. 15 shows a sponge member 480 to be used in building a transfer sandwich for electroblotting in order to achieve a uniform pressure over the whole surface of the electrophoresis gel unit 35 and the membrane unit 400 during the electrotransfer. In the disclosed embodiment, the sponge member 480 is provided with optional alignment holes to cooperate with the alignment structure of the panel 510a. The sponge member 480 may be comprised of any suitable material with appropriate material characteristics.

Figure 16:
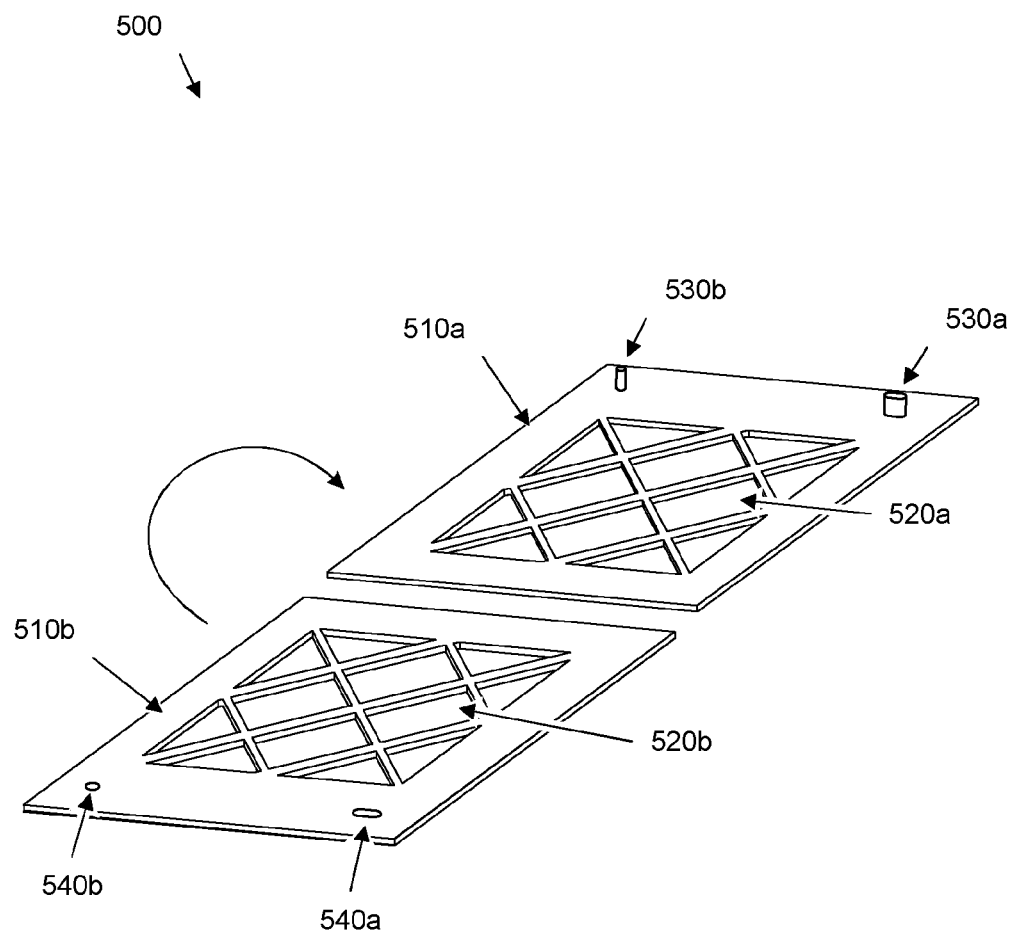
FIG. 16 shows an example of a sandwich holder for electroblotting.

As mentioned, the provision of corresponding alignment structures on the gel support frame 30 and the rigid blot frame 420 makes it possible to transfer sample constituents from the gel member 36 to the blot membrane 410 according to a known geometrical relationship, e.g. by electroblotting. FIG. 16 shows an example of a sandwich holder 500 for electroblotting, comprising a first and a second support panel 510a and 510b respectively. Each one of the two panels 510a and 510b comprises a grid section 520a and 520b respectively to allow essentially unrestricted fluidic and electrical contact with a transfer sandwich formed in-between the two panels 510a and 510b. The first support panel is provided with an alignment structure 530a and 530b that is formed to be complementary to the alignment tag 180 of the support frame 30 and the alignment tag 440 of the rigid blot frame 420 in order to establish a known geometrical relationship between the electrophoresis gel unit 35 and the membrane unit 400 as discussed above. In the disclose embodiment, the alignment structure is comprised of an elongated pin 530a and a circular pin 530b, in a corresponding arrangement as the alignment structure 330 of the electrophoresis tray 300 shown in FIG. 6, and both the electrophoresis gel unit 35 and the membrane unit 400 are formed to be mutually aligned using said pins. In this way, the sample constituents of the electrophoresis bands of the electrophoresis gel unit 35 are transferred to corresponding geometrical positions of the membrane unit 400 with respect to the alignment structures. Hence in case the electrophoresis gel unit 35 and the membrane unit 400 are imaged using an imager comprising a complementary alignment structure, the images would essentially be aligned.

FIGS. 17a to 17e schematically show the assembly of a transfer sandwich for electroblotting using the sandwich holder 500:

1. A first sponge member 480 is placed on the first panel 510a in order to achieve a uniform pressure over the whole surface of the electrophoresis gel unit 35 and the membrane unit 400 during the electrotransfer. In the disclosed embodiment, the sponge member is provided with optional alignment holes to cooperate with the alignment structure of the panel 510a. (FIG. 17a)
2. Membrane unit 400 is placed on top of the sponge member 480. (FIG. 17b)
3. Electrophoresis gel unit 35 is placed on top of the membrane unit 400 so that the gel member 36 is placed in proper contact with the membrane 410. (FIG. 17c)
4. A second sponge member 480 is placed on the electrophoresis gel unit 35, (FIGS. 17d) and
5. The second panel 510b is placed on top of the sandwich to keep it together during the electroblotting transfer process. (FIG. 17e)

Optionally there may be provided a sheet of filter paper or similar fine porous material in between each sponge member 480 and each one of the membrane unit 400 and the electrophoresis gel unit 35.

In the disclosed embodiment, the two panels 510a and 510b are shown as independent panel members with no interconnection features or the like. However in many applications, it may be suitable to have clamping features or the like (not shown) to hold the assembled sandwich together. Such clamping features may be integrated features of one or both of the panels 510a-b or it may be formed as one or more separate features. By selecting suitable material properties for the sponge members 480 and a suitable predefined distance between the panels 510a-b, it may be possible to achieved a well-defined compression between the electrophoresis gel unit 35 and the membrane unit 400 during the electrotransfer process.

After the electrotransfer process, the membrane unit 400 is further processed by probing and imaging steps, wherein the handling of the membrane is greatly facilitated by the presence of the rigid blot frame 420 which both serves as a handle for gripping the membrane, but also prevents folding and twisting of the thin membrane. Moreover, the alignment structure 450a-b and the information code field 460 of the blot frame 420 provides unique information about correct orientation of the membrane and essentially prevents that the membrane by mistake is processed upside down or the like. In order to further ensure proper orientation of the membrane unit 400 during the probing process, there may be provided a probing chamber with a corresponding alignment structure as disclosed above. Further, the blot frame 420 may facilitate the steps of the probing process, as it will keep the membrane 410 essentially flat so that it can be more easily submerged in the probing media etc. It is further possible to mechanically hold down the membrane unit 400 e.g. against the bottom of a probing chamber by mechanically pressing down the blot frame 420, thus not contacting the membrane.

Figure 18:
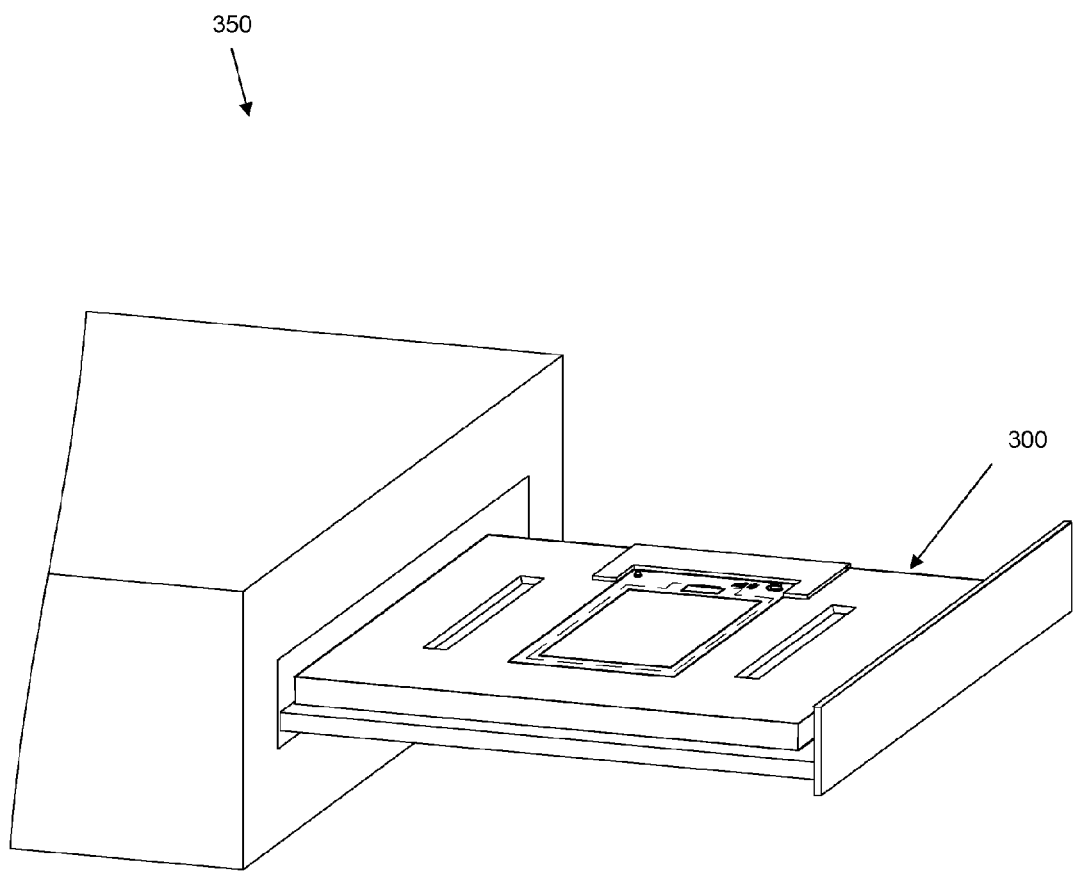
FIG. 18 schematically shows a membrane unit placed on a tray of a combined electrophoresis and imaging apparatus.

As previously mentioned, by providing alignment structures on both the electrophoresis gel unit 35 and the membrane unit 400, may be used to provide for aligned imaging of the two, whereby the following image evaluation steps may be greatly facilitated. Depending on the accuracy of the alignment features, and the requirements of the image evaluation steps, the mechanical alignment may be used directly for evaluation, or it may serve as a very good starting point for a refined electronic alignment e.g. by image analysis software. FIG. 18 schematically shows a membrane unit 400 placed on a tray 300 of a combined electrophoresis and imaging apparatus 350 as previously discussed with reference to FIG. 11, wherein the alignment structure of the tray is used to also align the membrane unit 400.

According to one embodiment, there is provided a method of running an electrophoresis experiment comprising the steps,
providing an electrophoresis cassette comprising a gel member in a housing with a front and a back face,
providing an electrophoresis tray arranged to support the electrophoresis cassette for running electrophoresis experiments, wherein the tray comprises a cassette support surface for supporting at least the separation zone of the electrophoresis cassette during electrophoresis, and wherein the cassette support surface is flanked by a pair of buffer pad holders each one arranged to hold a buffer pad in a mating position with respect to buffer connection sections at the back face of the electrophoresis cassette,
arranging buffer pads in the buffer pad holders,
placing the electrophoresis cassette in position on the tray,
loading sample into one or more sample wells of the electrophoresis cassette, and
applying an electrical field between the buffer pads.

Figure 19A:
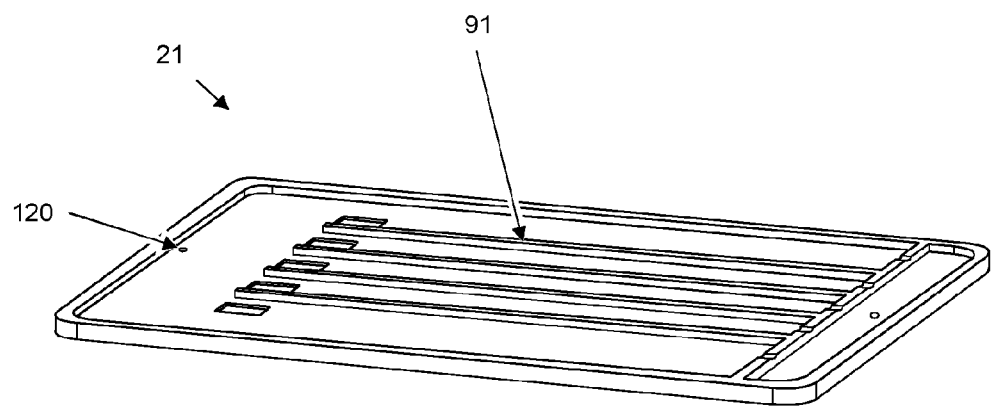
FIGS. 19a and 19b show two schematic examples of a cassette housing providing for separate electrophoresis lanes.
Figure 19B:
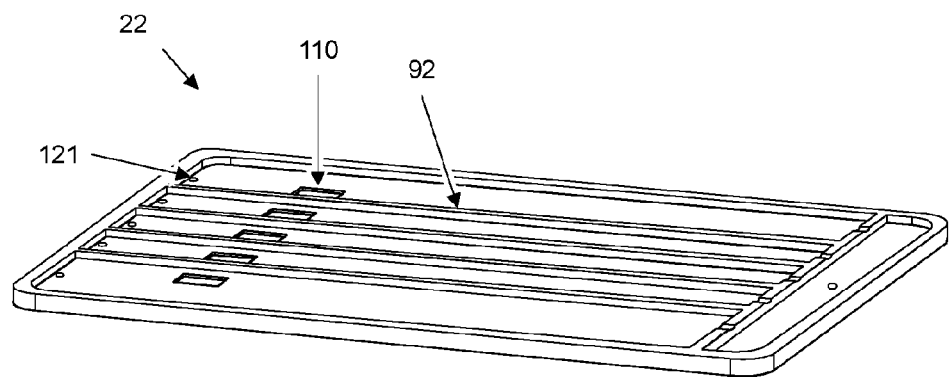

FIGS. 19a and 19b show two schematic examples of a cassette housing 21 and 22 respectively providing for separate electrophoresis lanes by the provision of longitudinal wall members 91 and 92 respectively. In the embodiment of FIG. 19a, the longitudinal walls 91 are terminated at the sample wells 110 leaving a common compartment at that end of the housing 21. Hence, a cassette 10 comprising the housing 21 may be filled through one single fill port 120 and all lanes will be filled with the same gel composition. In the embodiment of FIG. 19b, the longitudinal walls 92 extends all the way to the rim 70 of the housing 22 thus creating separate gel compartments for each lane and each lane comprising its own fill port 121. The cassette housings 21 and 22, respectively, may be combined with detachable gel support frame 30, a section-wise removable backing film 40 and a removable sample well cover 50 according to anyone of the above embodiments.

FIGS. 20a-h show another schematic embodiment of an electrophoresis cassette 600, comprising a rigid gel support frame 610, a removable top film 620 with a sample loading opening 625, a removable sample opening cover 630 and a section-wise removable backing film 640. As is disclosed in FIGS. 20e and 20g, the cassette 600 further comprises a sample well former 650 that is formed to be arranged on top of the sample loading opening 625 when the opening cover 630 has been removed so that it comes into contact with the surface of a gel that is molded in the cassette to form one or more sample wells for loading sample to the cassette 600. The well former 650 may have a suitable number of wells, and there may be provided sample well loaders with different numbers of wells in order to provide a flexible solution.

The gel support frame 610 comprises an outer frame 660 of a predefined height, which further defines the height of the gel molded in the cassette 610. The top face of the gel support frame 610 is comprised of a top rim 670 surrounding the gel compartment 680, defined by a through opening in the gel support frame 610. The bottom face of the gel support frame 610 comprises a corresponding bottom rim 690. The top film 620 is detachably attached to the top rim 670 and the section-wise removable backing film 640 is detachably attached to the bottom rim 690 thus enclosing the gel compartment 680 at the top and bottom respectively to allow a molding of an electrophoresis gel member 700 therein. In order to establish a strong interconnection between the gel support frame 610 and the gel member 700 molded therein, the gel support frame 610 is provided with a gel attachment rim 710 that extends inwards from the outer frame 660 into the gel compartment. The gel attachment rim 710 is thin compared to the outer frame 660 and thus the gel member 700, in order to be covered on one side or fully incorporated into the gel member. According to the disclosed embodiment, the gel attachment rim 710 may further comprise interconnection structures 720 which enhances the mechanical interconnection of the gel to the attachment rim 710. The interconnection structures 720 may e.g. be through holes in the attachment rim 710, or it may be cutouts in the same, or a range of other structures that will be filled by gel after molding to promote interconnection.

The gel support frame 610 is provided with a predefined alignment structure in the form of alignment holes 191a to 191c, arranged to ensure that the cassette 600 and/or the support frame 610 is properly aligned with respect to a complementary alignment structure e.g. comprising 3 pins, in an electrophoresis apparatus or the like. As is disclosed in FIGS. 20a-h there are provides corresponding alignment holes 191a to 191c in the top film 620, but no corresponding holes in the buffer sections 641a and 641b of the section-wise removable backing film 640. In this way, a user is prevented from fitting the cassette 600 e.g. in an electrophoresis apparatus without first removing the buffer sections 641a and 641b of the section-wise removable backing film 640 in order to uncover the alignment structure in the form of alignment holes 191a to 191c. Thus avoiding the risk of running the electrophoresis process with the protective buffer sections 641a and 641b preventing the gel member from electrochemical contact with buffer pads or the like.

Like in the cassette 10 the backing film 640 is section-wise removable, and comprises two buffer sections 641a and 641b arranged to expose the end sections of the gel member 700 in order to put the gel member into contact with respective buffer pads or the like (not shown), and a central section 641c arranged to provide access to the separation-zone after the electrophoretic separation, much like above. By selecting suitable material combinations and adhesive technology, the backing film 640 may be attached onto the bottom rim 690 such that the respective sections 641a-c can be removed e.g. by an operator grabbing and pulling a respective peel tab 642a-c.

Figure 20F:
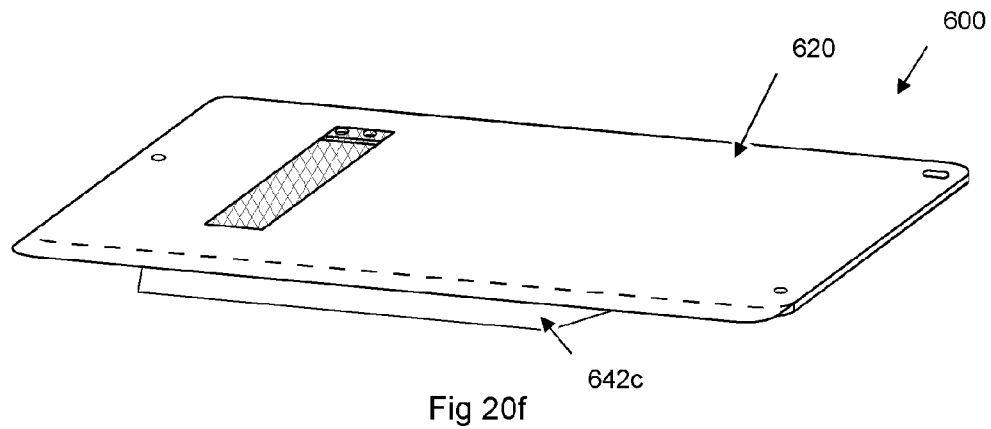
Figure 20G:
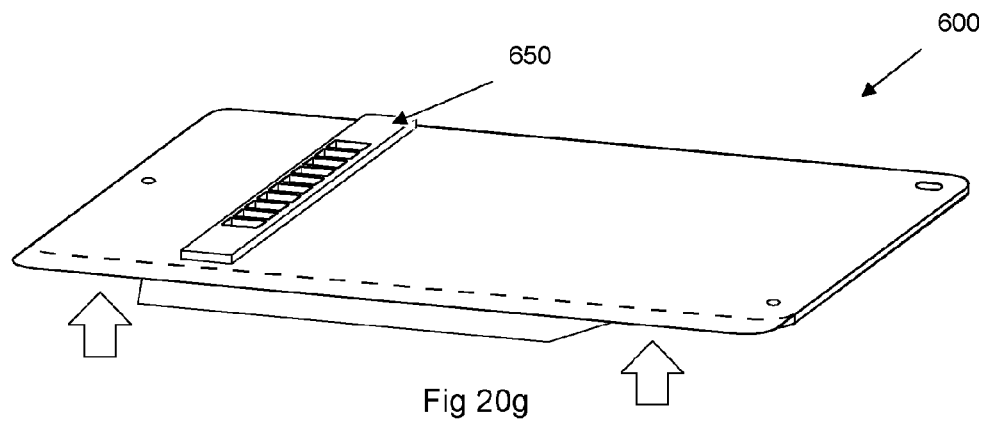
Figure 20H:
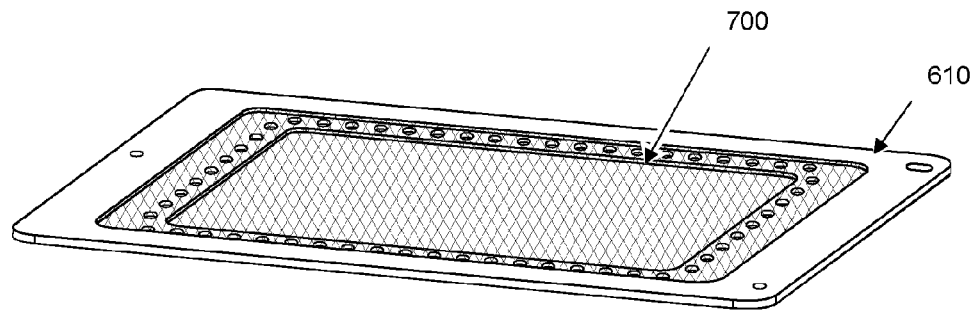

FIG. 20f shows the electrophoresis cassette 600 in enabled state with the opening cover 630 removed and FIG. 20g shows the electrophoresis cassette 600 with the well former 650 in place whereby samples may be loaded to perform electrophoretic separation. Moreover in both FIGS. 20f and 20g the two buffer sections 641a and 641b are removed and in FIG. 20g connection to respective bufferpad is indicated by arrows. After separation is completed, the top film 620 and the central section 641c are removed to provide access to the separation-zone from both top and bottom, while the gel member is still attached to the gel support frame 610.

FIGS. 21a-h show another schematic embodiment of an electrophoresis cassette 730 that is similar to the embodiment of FIGS. 20a-h, comprising a rigid gel support frame 610, a section-wise removable top film 740 and a removable backing film 750. As is disclosed in FIGS. 20a and 20b, the cassette 730 further comprises a combined sample well former and buffer compartment 760 and a buffer compartment 770 that are formed to be arranged on top of electrophoresis cassette 730 when a first and a second section 741a and 741b of the section-wise removable top film 740 has been removed so that they come into contact with the surface of a gel that is molded in the cassette 730 to form one or more sample wells for loading sample to the cassette 730 and buffer reservoirs on top of the gel member 700 as is sown in FIG. 21g. The well former 760 may have a suitable number of wells, and there may be provided sample well loaders with different numbers of wells in order to provide a flexible solution.

Figures 21A, 21B:
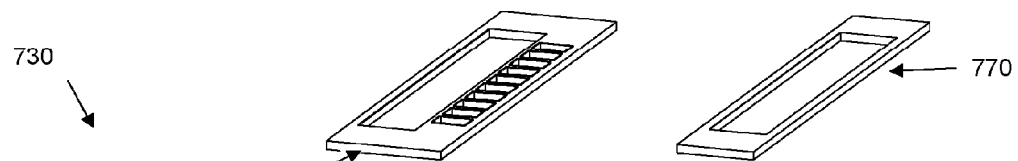
FIGS. 21a-h show another schematic embodiment of an electrophoresis cassette
Figure 21C:
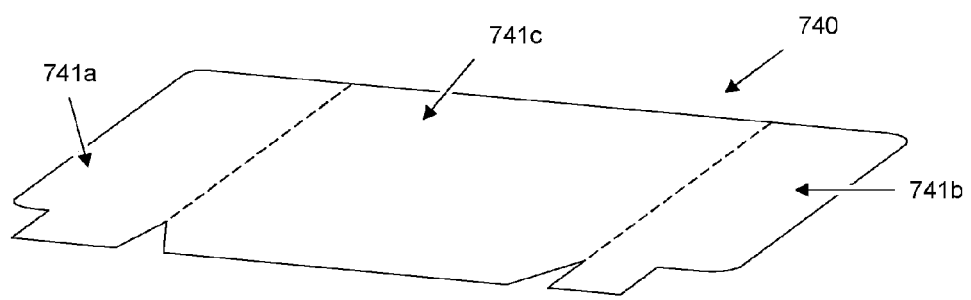
Figure 21D:
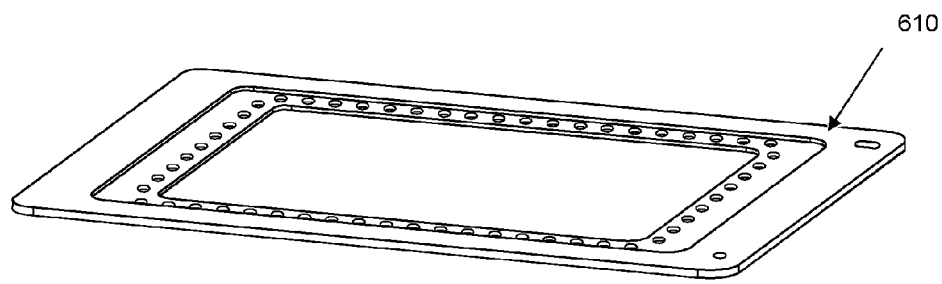
Figure 21E:
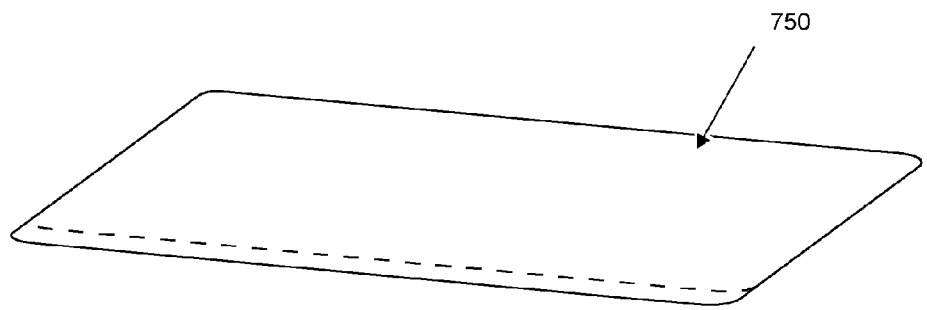
Figure 21F:
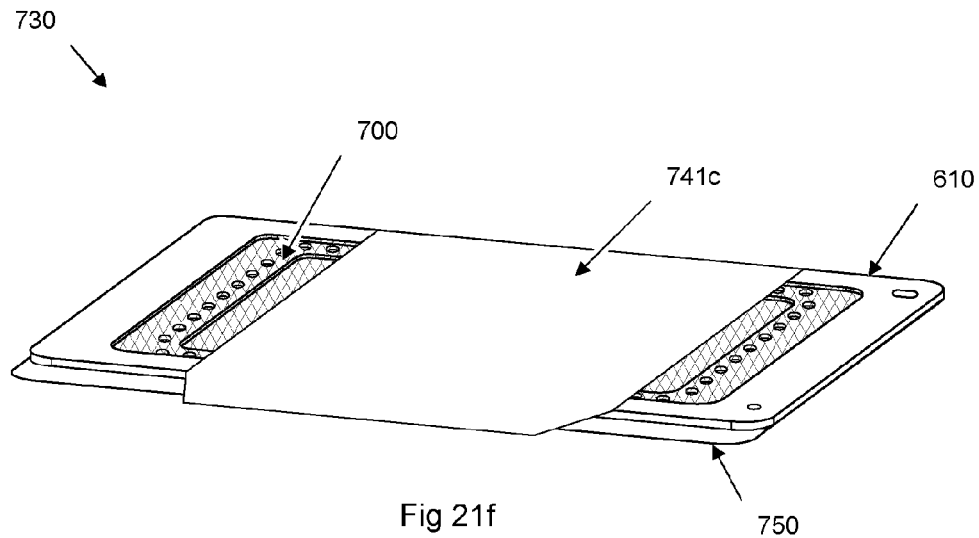
Figure 21G:
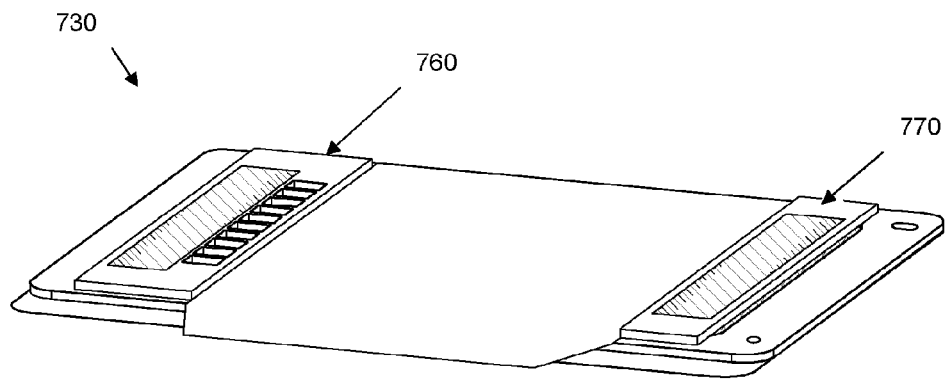
Figure 21H:
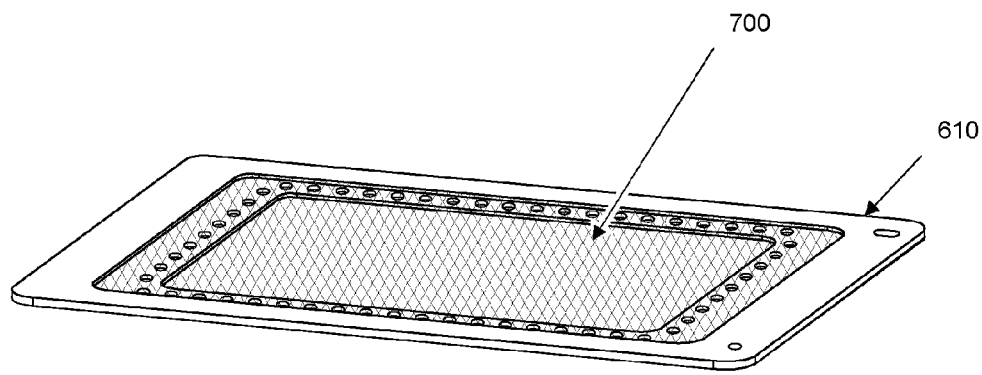

Thus, in the embodiment of FIG. 21a-h, the electrophoresis cassette 730 is designed with the buffers on top of the gel member 700, and the buffer may either be provided in the form of a gel pad or possibly in liquid form. After the electrophoretic separation, section 741c of the section-wise removable top film 740 and the backing film 750 are removed and the gel member 700 stays supported by the support frame 610 as is shown in FIG. 21h.

Figure 22A:
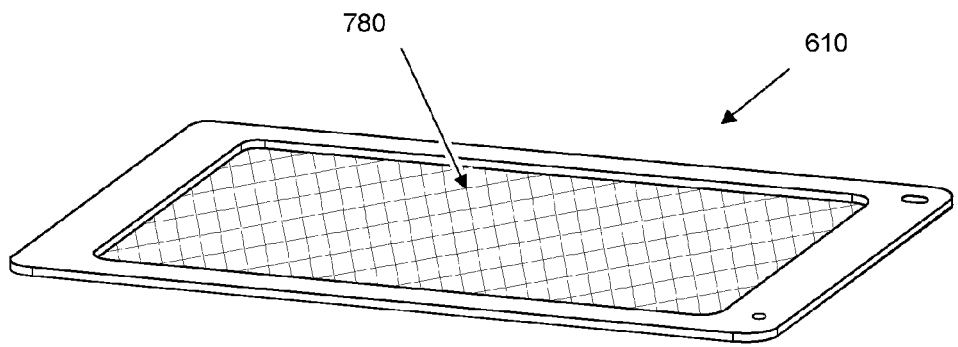
FIG. 22 schematically shows a rigid gel support frame, with a permeable or semi permeable backing
Figure 22B:
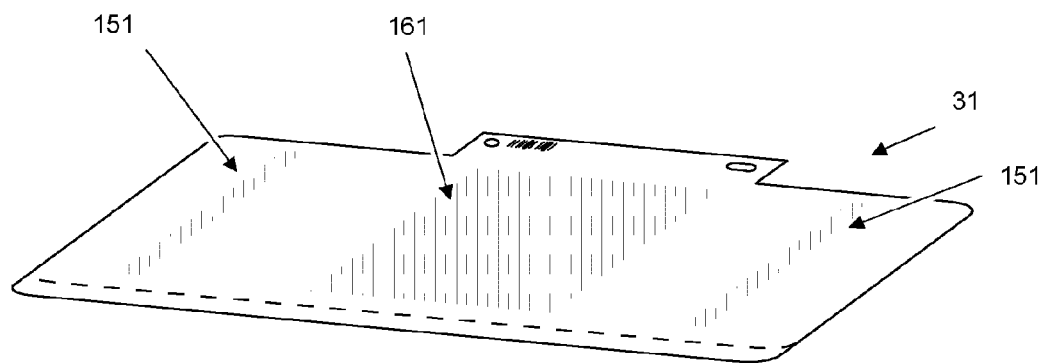

FIG. 22a schematically shows a rigid gel support frame 610, with a permeable or semi permeable backing 780 arranged to establish a strong interconnection with the gel member and actually act as a reinforcement of the same. The permeable backing 780 may e.g. be a web of a suitable electrically insulating material, a perforated or porous sheet or film that can provide adequate electrochemical contact with the gel member from either side. In the disclosed embodiment, the permeable backing 780 is shown attached to a support frame 610, but it may be attached to any suitable support structure as disclosed herein. Moreover, the permeable backing 780 may be formed to provide further structural support in addition to the support frame. FIG. 22b schematically shows a support frame 31 of film type with permeable backing 780 attached over the openings in the film or formed as an integral part thereof, e.g. by providing perforated or by other means modified sections 151 and 161 to provide adequate electrochemical contact with the gel member.

Figures 23A, 23B:
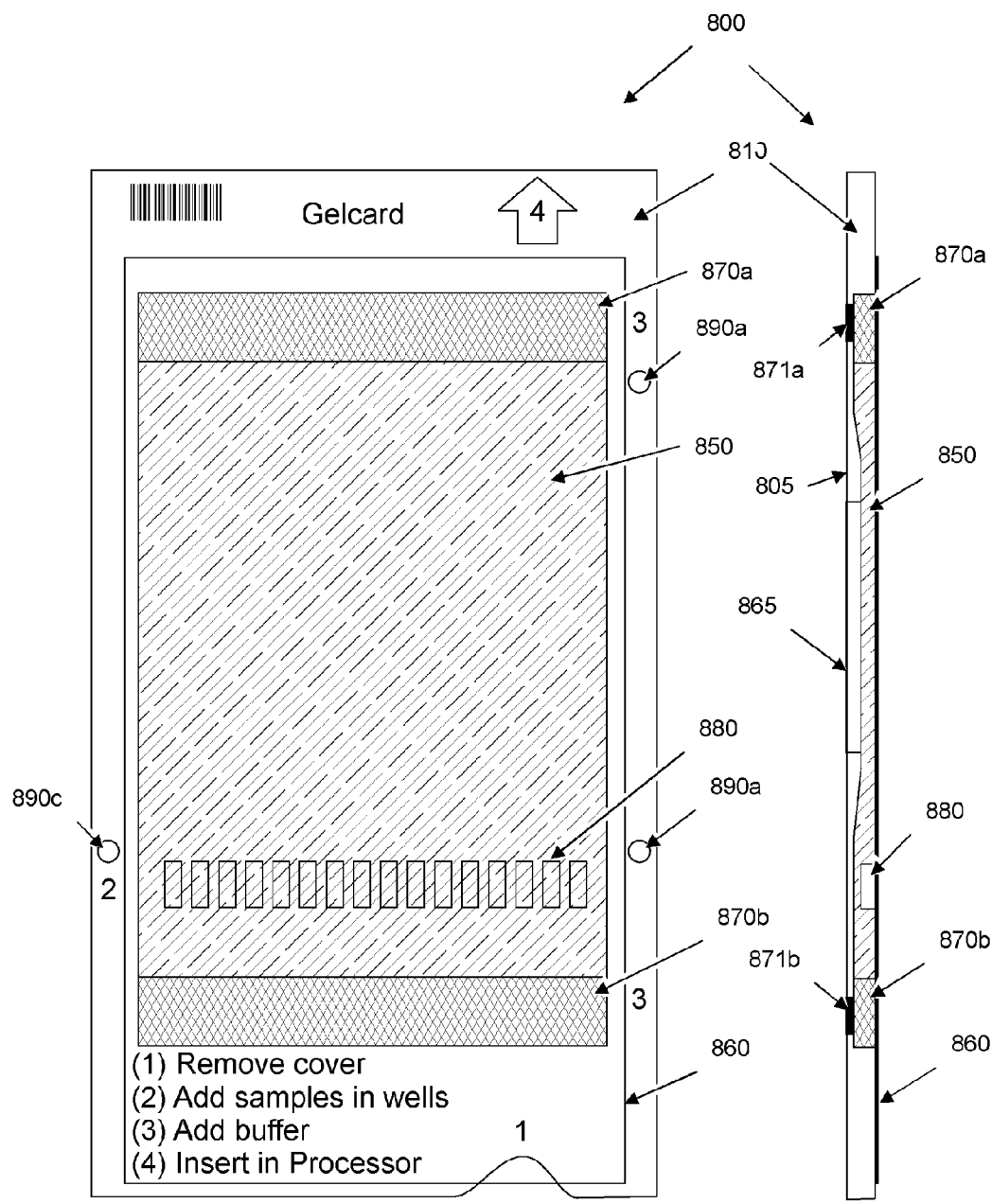

FIGS. 23a-23g shows a schematic protein analysis concept comprising a "Gelcard" 800, a "Blotcard" 900 and a "Transfercard" 820 with integrated electrophoresis and immunoblot functionalities. The cards 800, 810 and 820 have a lot of features in common with the above embodiments, and many features shown with respect to either embodiment may likewise be implemented in other embodiments. FIG. 23a shows the Gelcard 800 in a top view, and FIG. 23b shows the same gelcard 800 in a schematic cross-sectional view adapted to show the integrated features of the card. The gelcard 800 comprises a rigid support frame 830 with a back wall 805 defining a recess forming a gel compartment for molding a gel member 850 therein. The top of the gel compartment 850 is closed by a cover film 860 removably attached to the top face of the support frame 830. The gelcard 800 further comprises integrated buffer pads 870a and 870b and associated electrodes 871a and 871b arranged to be connected to a power source to drive the electrophoresis process, e.g. by connector surfaces at the back face of the gelcard 800. The buffer pads 870a and 870b may e.g. be of sponge type arranged to be soaked with buffer soultion during the process of preparing the gelcard 800 for the electrophoresis process, alternatively, the buffer pads may be "prefilled" with buffer, e.g. in gel-form or the like. In the disclosed embodiment, the gel member is designed with reduced thickness at the separation-zone compared to the sample loading and buffer interaction segments. Sample loading wells 880 are formed directly in the gel, e.g. by providing mold structures attached to the cover film 860 or the like.

The support frame 830 of the gelcard 800 further comprises a back wall 805 with a removable section 865 to provide access to the back face of the gel member 850. Like the above embodiments, the gelcard 800 comprises an alignment structure in the form of 3 alignment holes 870a-870c near the edges to allow proper alignment with the Blotcard 810 and the Transfercard 820 by means of mutual alignment structures. In order to further facilitate for a user of the electrophoresis system comprising the gelcard 800, it is provided with printed operation instructions on one or more faces thereof. The operation instructions are further complemented by number indicators at relevant locations on the face of the gelcard 800. The sequence for using the gelcard 800 comprises the steps:
1. Remove cover 860
2. Add samples in wells 880
3. Add buffer in buffer pads 870a and 870b
4. Insert in processor apparatus for electrophoretic separation.

FIG. 23c shows the blotcard 900 in a top view, and FIG. 23d shows the same blotcard 900 in a schematic cross-sectional view adapted to show the integrated features of the card.

The blotcard 900 comprises a rigid frame 910 of a shape and structure that corresponds to the gelcard 800. A blot membrane 920 is attached to one side of the rigid frame 910, covered on one side of a thin cover film 850 to be removed before the transfer steps, and by a buffer pad 930 on the back face thereof.

Figures 23E, 23F:
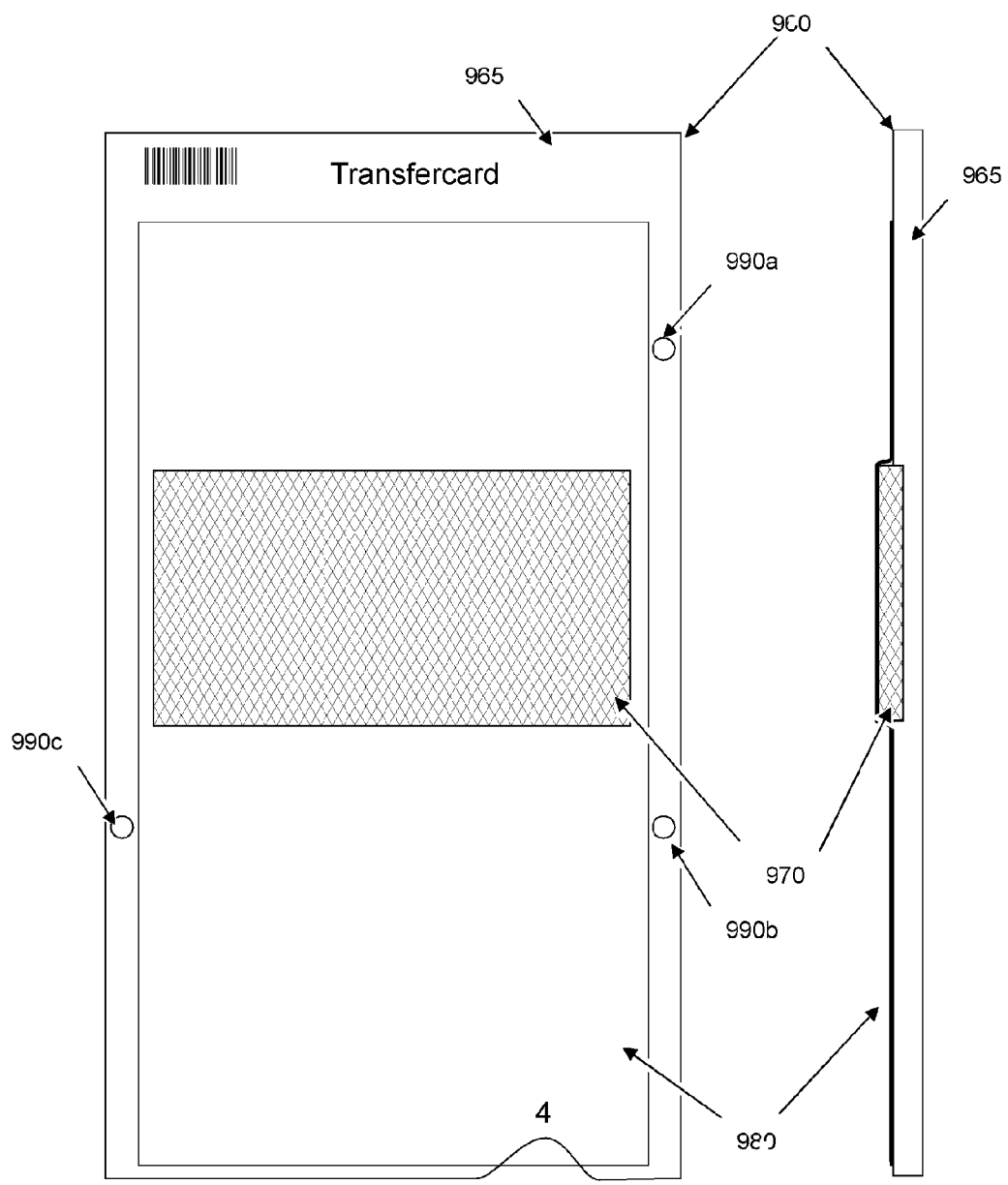
Figure 23G:
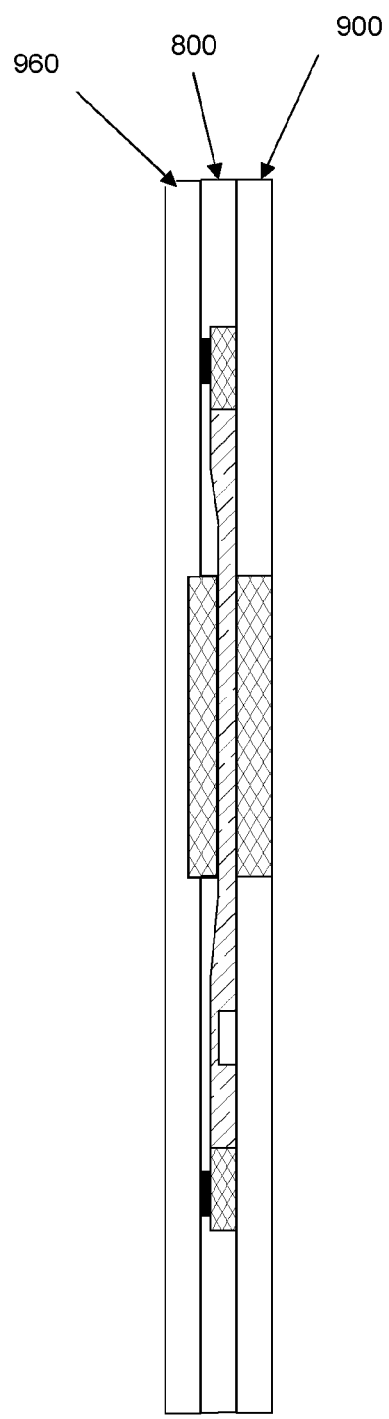

FIG. 23e shows the transfercard 960 in a top view, and FIG. 23f shows the transfercard 960 in a schematic cross-sectional view adapted to show the integrated features of the card. The transfercard 960 comprises a rigid frame 965 of a shape and structure that corresponds to the gelcard 800 and the blotcard 900. A buffer pad 970 is arranged on the front face of the rigid frame 965 and is covered by a thin cover film 980. buffer pad 930 as will be evident from FIG. 23g, the buffer pad 970 of the transfer card 960 is arraned to extend a distance from the front face of the rigid frame 965 in order to be arranged in electrochemical contact with the gel through the removable section 865 of the gelcard back wall 805

Like the gelcard 800, the blotcard 900 and the transfer card 960 comprises an alignment structure in the form of 3 alignment holes 940a-940c and 990a-990c respectively, near the edges to allow proper alignment between the Gelcard 800, the blotcard 900 and the Transfercard 960 by means of mutual alignment structures. Like for the gelcard 800, the blotcard 900 is provided with printed operation instructions on one or more faces thereof The sequence for using the blotcard 900 comprises the steps:

1. Remove cover 950,
2. Dock to processed Gelcard to front face of gel card 800 using alignment structures.
3. Remove the removable section 865 of the gelcard back wall 805 to provide access to the back face of the gel member 850
4. Remove transfer card 960 cover 980
5. Dock transfercard 960 to back face of gelcard 800 using alignment structures.
6. Insert into Blotter (not shown) for blot processing
7. Undock all
8. Remove buffer pad 930 of blotcard to free the membrane.
9. Insert into incubator
10. Insert into processor for imaging of blot results.

The stack of cards provided up to step 5 is schematically disclosed in FIG. 25g. From this it can be seen that the stack of cards provides a transfer stack for aligned transfer of separated sample from the separation zone to the blot membrane 920 of the blotcard like in the above embodiments, but with the difference that the disclosed embodiment is arranged for semidry electro transfer, wherein the buffer pads 930 and 970 of the blotcard 900 and the transfercard 960 respectively provides the desired buffer conditions for the electrotransfer process.

According to one embodiment, the stack of cards are provided with integrated mutual alignment structures of snap lock type to further facilitate handling during the process of electroblotting.

Like in the above embodiment, the electrophoresis cassette and the membrane unit of the present invention may be referred to as an electrophoresis gel card and a blot membrane card respectively.

According to one embodiment there is provided an electrophoresis system comprising:
at least one type of electrophoresis gel card,
at least one type of blot membrane card,
an electrophoresis apparatus for running electrophoresis experiments using the electrophoretic gel card,
a blot transfer unit for transfer of separated sample from the electrophoresis gel card to the blot membrane card,
an imaging apparatus for recording images of separated sample in the electrophoresis gel card and the blot membrane card, wherein;
the electrophoresis gel card and the blot membrane card each comprises a rigid support provided with an alignment structure defining a positional reference for mutual alignment during transfer, and for alignment with respect to a complementary alignment structure in the imaging apparatus to provide mechanically aligned images of separated sample in the electrophoresis gel card and the blot membrane card.

In order to provide for mutual alignment, the electrophoresis system may comprise a transfer holder with a complementary alignment structure for holding the electrophoresis gel card and the blot membrane card in mutual aligned position in the blot transfer unit. One schematic example of such a transfer holder 500 is shown in FIGS. 16 and 17. As disclosed above the electrophoresis gel card may comprise a housing with removable members to expose both the first and second face of the gel member to allow blot transfer of separated sample while the gel member is attached to the rigid support. The electrophoresis gel card may further comprise at least one removable member that has to be removed in order run at least one step in the electrophoresis workflow, and wherein the removable member is formed to at least partially block the alignment structure to prevent running said step without first removing the removable member. This is e.g. schematically shown in the embodiment of FIG. 20a-20h. The electrophoresis gel card may be provided with a precast gel, or optionally, the gel card is provided so that a user may mold a gel in the gel card himself. According to one embodiment, as is schematically disclosed in FIG. 25b the electrophoretic gel card may comprise integrated buffer compartments and optionally electrodes.

In order to provide unique orientation and to avoid improper positioning, the alignment structures of the electrophoresis gel card and the blot membrane card are formed to define a unique orientation of respective card. According to one embodiment, the alignment structures of the electrophoresis gel card and the blot membrane card comprises at least one alignment hole and wherein a complementary alignment structure comprises a complementary alignment pin.

In order to provide unique identification, the electrophoresis gel card and the blot membrane card may each comprise an identification code, and the identification codes may be arranged to be simultaneously read when mutually aligned for transfer to establish a unique link between said cards, and the system may be arranged to store said link. The identification code may e.g. be a machine readable code as a bar-code, matrix-code or the like, and provide the user and/or instruments with relevant information. According to one embodiment, the imaging apparatus may be arranged to read the identification code of a card arranged for imaging, and in one embodiment, the imaging apparatus may be arranged to select an imaging protocol based on the registered identification code of a card arranged for imaging.

According to one embodiment the electrophoresis gel card may comprise an identification code that is arranged to be transferred to a blot membrane card at the blot transfer. The identification code may be electrochemically transferred from the electrophoresis gel card to the blot membrane card.

According to one embodiment there is provided a separation and identification method comprising the steps:
separating a sample, by electrophoresis, in an electrophoresis gel card comprising a rigid support provided with an alignment structure defining a positional reference,
acquiring an image of the sample separated in the electrophoresis gel card using an imager with a complementary alignment structure, and wherein the alignment structure of the electrophoresis gel card is arranged in alignment with the complementary alignment structure,
transferring sample constituents from the gel card to a blot membrane card comprising a rigid support provided with an alignment structure defining a positional reference, wherein the electrophoresis gel card and the blot membrane card are arranged in mutual alignment by means of the alignment structures,
acquiring an image of transferred sample constituents on the blot transfer card wherein the alignment structure of the blot transfer card is arranged in alignment with the complementary alignment structure of the imager, and analyzing the images comprising the step of correlating the images based on the mutual alignment.

The concept of providing a support frame for the gel member and/or blot membrane thus provides a whole range of benefits for a protein analysis system based on electrophoresis and immunoblotting.

What is claimed is:

1. An electrophoresis gel cassette comprising a first face wall member, a second face wall member, and one or more side wall members defining a gel compartment for a gel member with a first face and a second face, wherein at least a section of each of the first face wall member and the second face wall member is removable to expose a section of both the first face and the second face of the gel member essentially corresponding to a separation zone while the gel member is preserved in the cassette, wherein at least one of the removable sections of the first face wall member and the second face wall member is formed of two or more laminated layers of plastic film, the two or more laminated layers of plastic film comprising a first layer and a second layer, wherein the first layer faces the gel compartment and has one or more openings formed therein which are covered by one or more peelable sections of the second layer.

2. The electrophoresis gel cassette according to claim 1, wherein the side wall members are formed integrally with one of the face wall members to form a cassette body.

3. The electrophoresis gel cassette according to claim 1, wherein the removable sections of the first face wall member and the second face wall member are provided with low gel adhesion properties with respect to the gel member.

4. The electrophoresis gel cassette according to claim 1, wherein at least one of the first face wall member and the second face wall member is provided with one or more removable sections arranged to expose a buffer contact section of the gel member.

5. The electrophoresis gel cassette according to claim 1, further comprising integrated buffer compartments.

6. The electrophoresis gel cassette according to claim 1, wherein at least one of the removable sections of the first face wall member and the second face wall member is formed as a rigid lid.

7. The electrophoresis gel cassette according to claim 6, wherein the first layer comprises a PET film with adhesive EVA layers applied to a first face and a second face of the first layer, and wherein the second layer comprises a PET film.

8. The electrophoresis gel cassette according to claim 1, wherein the first layer comprises a rigid polymer film with adhesive layers applied to a first face and a second face of the first layer, and wherein the second layer comprises a rigid polymer film.

9. The electrophoresis gel cassette according to claim 1, further comprising a precast gel.

10. The electrophoresis gel cassette according to claim 1, wherein at least one of the first face wall member and the second face wall member comprises an optically transparent material to allow imaging of the gel member without opening the cassette.

11. The electrophoresis gel cassette according to claim 1, further comprising an alignment structure defining a positional reference for alignment of the cassette.

12. The electrophoresis gel cassette according to claim 1, further comprising an identification code.

13. The electrophoresis gel cassette according to claim 5, further comprising electrodes.

* * * * *